United States Patent
Lee et al.

(10) Patent No.: US 10,324,065 B2
(45) Date of Patent: Jun. 18, 2019

(54) ULTRASOUND DIAGNOSTIC APPARATUS, ULTRASOUND IMAGE CAPTURING METHOD, AND COMPUTER-READABLE RECORDING MEDIUM

(71) Applicant: SAMSUNG ELECTRONICS CO., LTD., Suwon-si (KR)

(72) Inventors: Hyoung-ki Lee, Seongnam-si (KR); Dong-geon Kong, Hwaseong-si (KR); Jun-ho Park, Hwaseong-si (KR); Ki-wan Choi, Anyang-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 478 days.

(21) Appl. No.: 14/590,118

(22) Filed: Jan. 6, 2015

(65) Prior Publication Data

US 2015/0192547 A1    Jul. 9, 2015

(30) Foreign Application Priority Data

Jan. 6, 2014    (KR) ................ 10-2014-0001503
Sep. 24, 2014    (KR) ................ 10-2014-0127687

(51) Int. Cl.
    *G01N 29/04*      (2006.01)
    *G01N 29/24*      (2006.01)
               (Continued)

(52) U.S. Cl.
    CPC ............ *G01N 29/04* (2013.01); *A61B 8/06* (2013.01); *A61B 8/08* (2013.01); *A61B 8/0891* (2013.01);
               (Continued)

(58) Field of Classification Search
None
See application file for complete search history.

(56) References Cited

U.S. PATENT DOCUMENTS 5,143,070 A     9/1992   Ophir et al.
5,329,930 A   *   7/1994   Thomas, III ........ G01S 15/8913
                                               600/443
(Continued)

FOREIGN PATENT DOCUMENTS

KR    10-2012-0008218 A    1/2012
WO    2011/007278 A2    1/2011
(Continued)

OTHER PUBLICATIONS

Song et al., IEEE Transactions on Medical Imaging, vol. 32, No. 8, Aug. 2013. "Comb-push ultrasound shear elastography (CUSE) with various ultrasound push beams."*

(Continued)

*Primary Examiner* — Katherine L Fernandez
*Assistant Examiner* — Yi-Shan Yang
(74) *Attorney, Agent, or Firm* — Sughrue Mion, PLLC

(57) ABSTRACT

An ultrasound diagnostic apparatus includes: a probe that includes a transducer array including transducers, which are activated as a first transducer group and a second transducer group, is configured to transmit ultrasound waves by at least one transducer included in the first transducer group and at least one transducer included in the second transducer group, and to detect echo signals from an object; and a controller configured to select a number of transducers to be activated in the first transducer group and in the second transducer group based on the object or a measurement result, generate echo images from the echo signals, and measure an object change movement speed, which is a speed at which a change in the object moves, from the echo images.

26 Claims, 17 Drawing Sheets

(51) Int. Cl.

| | | |
|---|---|---|
| *A61B 8/08* | (2006.01) | |
| *G01N 29/06* | (2006.01) | |
| *G01N 29/07* | (2006.01) | |
| *G01N 29/34* | (2006.01) | |
| *A61B 8/06* | (2006.01) | |
| *A61B 8/00* | (2006.01) | |
| *G01S 7/52* | (2006.01) | |
| *B06B 1/02* | (2006.01) | |
| *G01N 29/26* | (2006.01) | |
| *G10K 11/34* | (2006.01) | |
| *G01S 15/89* | (2006.01) | |

(52) U.S. Cl.
CPC ............ *A61B 8/4488* (2013.01); *A61B 8/485* (2013.01); *A61B 8/488* (2013.01); *A61B 8/5207* (2013.01); *A61B 8/5223* (2013.01); *A61B 8/565* (2013.01); *B06B 1/0215* (2013.01); *G01N 29/0654* (2013.01); *G01N 29/07* (2013.01); *G01N 29/24* (2013.01); *G01N 29/2437* (2013.01); *G01N 29/262* (2013.01); *G01N 29/343* (2013.01); *G01S 7/52022* (2013.01); *G01S 7/52042* (2013.01); *G01S 7/52085* (2013.01); *G10K 11/345* (2013.01); *G10K 11/346* (2013.01); *A61B 8/00* (2013.01); *A61B 8/4405* (2013.01); *A61B 8/4472* (2013.01); *A61B 8/469* (2013.01); *B06B 2201/76* (2013.01); *G01N 2291/02475* (2013.01); *G01N 2291/044* (2013.01); *G01N 2291/106* (2013.01); *G01S 15/8915* (2013.01)

(56) References Cited

U.S. PATENT DOCUMENTS

| | | | |
|---|---|---|---|
| 5,606,971 A | 3/1997 | Sarvazyan | |
| 5,810,731 A | 9/1998 | Sarvazyan et al. | |
| 6,561,981 B2 | 5/2003 | Bonnefous | |
| 6,728,515 B1* | 4/2004 | Wooh ................... | H01Q 3/2682 455/67.11 |
| 7,252,004 B2 | 8/2007 | Fink et al. | |
| 7,374,538 B2 | 5/2008 | Nightingale et al. | |
| 8,118,744 B2 | 2/2012 | Palmeri et al. | |
| 8,225,666 B2 | 7/2012 | McAleavey | |
| 8,235,898 B2 | 8/2012 | Bae et al. | |
| 2005/0252295 A1* | 11/2005 | Fink .................. | A61B 8/08 73/603 |
| 2011/0066030 A1* | 3/2011 | Yao .................. | A61B 8/485 600/438 |
| 2011/0270136 A1* | 11/2011 | Vitek .................. | A61N 7/02 601/2 |
| 2012/0116220 A1* | 5/2012 | Burcher .............. | A61B 5/0048 600/438 |
| 2012/0302883 A1 | 11/2012 | Kong et al. | |
| 2013/0035582 A1* | 2/2013 | Radulescu ............. | A61N 7/02 600/411 |
| 2013/0123630 A1 | 5/2013 | Freiburger et al. | |
| 2013/0131511 A1 | 5/2013 | Peterson et al. | |
| 2013/0218012 A1* | 8/2013 | Specht .................. | A61B 8/485 600/438 |
| 2013/0317362 A1* | 11/2013 | Shi ....................... | A61B 5/0051 600/438 |
| 2014/0018679 A1* | 1/2014 | Chen ................... | A61B 8/085 600/438 |
| 2014/0046173 A1* | 2/2014 | Greenleaf ............. | G01N 21/17 600/411 |

FOREIGN PATENT DOCUMENTS

| | | |
|---|---|---|
| WO | 2012/085812 A2 | 6/2012 |
| WO | 2012116364 A1 | 8/2012 |

OTHER PUBLICATIONS

Communication dated Jul. 18, 2016, issued by the Korean Intellectual Property Office in counterpart Korean Application No. 10-2014-0127687.

International Search Report dated Apr. 9, 2015 issued by International Searching Authority in counterpart International Application No. PCT/KR2015/000118.

Written Opinion dated Apr. 9, 2015 issued by International Searching Authority in counterpart International Application No. PCT/KR2015/000118.

* cited by examiner

| PATIENT | PART | FIRST MOVEMENT SPEED |
|---------|--------|----------------------|
| A | LIVER | K |
| B | KIDNEY | L |

ULTRASOUND DIAGNOSTIC APPARATUS, ULTRASOUND IMAGE CAPTURING METHOD, AND COMPUTER-READABLE RECORDING MEDIUM

CROSS-REFERENCE TO RELATED APPLICATIONS

This application claims priority from Korean Patent Application No. 10-2014-0001503, filed on Jan. 6, 2014, and Korean Patent Application No. 10-2014-0127687, filed on Sep. 24, 2014, in the Korean Intellectual Property Office, the disclosures of which are incorporated herein in their entireties by reference.

BACKGROUND

1. Field

Apparatuses and methods consistent with exemplary embodiments relate to an ultrasound diagnostic apparatus, an ultrasound image capturing method, and a computer-readable recording medium which stores a computer program for executing the ultrasound image capturing method.

2. Description of the Related Art

Ultrasound diagnostic apparatuses transmit an ultrasound signal, generated by a transducer of a probe, onto an object and receive information of an echo signal reflected from the object, thereby obtaining an image of an object. In particular, ultrasound diagnostic apparatuses are used for the medical imaging, detecting a foreign material, and assessing an injury. Ultrasound diagnostic apparatuses have stabilities higher than those of diagnostic apparatuses using X-rays, display an image in real time, and are safe because there is no exposure to radioactivity, and thus may be widely used along with other image diagnostic apparatuses.

SUMMARY

According to one or more exemplary embodiments, an ultrasound diagnostic apparatus includes: a probe that includes a transducer array including transducers, which are activated as a first transducer group and a second transducer group, is configured to transmit ultrasound waves by at least one transducer included in the first transducer group and at least one transducer included in the second transducer group, and to detect echo signals from an object; and a controller configured to select a number of transducers to be activated in the first transducer group and in the second transducer group based on the object or a measurement result, generate echo images from the echo signals, and measure an object change movement speed, which is a speed at which a change in the object moves, from the echo images.

The probe may transmit an ultrasound wave by at least one transducer included in the first transducer group and detect an echo signal from the object, and, after a lapse of a time interval, transmit an ultrasound wave by at least one transducer included in the second transducer group and detect an echo signal from the object, and the time interval may be determined based on the object or the measurement result.

The probe may transmit an ultrasound wave by at least one transducer included in the first transducer group at a first activation position and detect an echo signal from the object, and transmit an ultrasound wave by at least one transducer included in the second transducer group at a second activation position, which has been spatially moved from the first activation position of the first transducer group at a first movement speed, and detect an echo signal from the object, and the first movement speed may be determined based on a characteristic of the object or the measurement result.

The ultrasound waves transmitted by the probe may include ultrasound plane waves.

The probe may move an ultrasound wave transmission position of a focus beam within each of the first transducer group and the second transducer group, transmit the ultrasound waves of the focus beam onto the object by the at least one transducer included in the first transducer group and the at least one transducer included in the second transducer group, and detect the echo signals corresponding to the ultrasound wave transmission position of the focus beam.

The first movement speed may be determined based on the characteristic of the object which is at least one of a medical record and an examination position of the object.

The controller may correct the first movement speed in response to a difference between the measured object change movement speed and the first movement speed being equal to or greater than a reference value, and the probe may transmit an ultrasound wave by at least one transducer included in a selected transducer group at a position which has been spatially moved from the first activation position at the corrected first movement speed, and detect an echo signal from the object.

The controller may calculate a variation image from two echo images which are sequentially captured, detect a change position of the object from the variation image, and calculate the object change movement speed by using the change position of the object.

The probe may further include multiplexers that connect a selected transducer to a signal transfer channel connected to the controller, and the transducer included in the first transducer group and the at least one transducer included in the second transducer group may be selected transducers selected by the multiplexers.

The first movement speed may be determined based on the measurement result, and the controller may measure the object change movement speed by using the probe, and determine the first movement speed based on the measurement result.

The probe may transmit the ultrasound waves onto the object to generate a shear wave in the object, the change in the object may include the shear wave, and the object change movement speed may include a propagation speed of the shear wave.

The probe may transmit the ultrasound waves of a focus beam onto the object to generate the shear wave.

The probe may generate the shear wave at a plurality of points of the object.

The controller may select the first transducer group, which is positioned at a first activation position at one end of the transducer array, and select the second transducer group, which is positioned at a second activation position at an opposing end of the transducer array in a lengthwise direction. The probe may transmit the ultrasound waves by using transducers of a corresponding first or second transducer group at a position which has been alternately moved from the first activation position and the second activation position toward a center of the transducer array at a first movement speed, and detect the echo signals from the object, and the first movement speed may be determined based on the object or the measurement result.

According to one or more exemplary embodiments, a method of capturing an ultrasound image, includes: selecting a number of transducers of a transducer array to be activated in a first transducer group and in a second transducer group, based on an object or a measurement result; transmitting ultrasound waves onto the object by at least one transducer included in the first transducer group and at least one transducer included in the second transducer group, to detect echo signals from the object; and measuring an object change movement speed that is a speed at which a change of the object moves, based on the echo signals.

The detecting the echo signals may include: transmitting an ultrasound wave by at least one transducer included in the first transducer group to detect an echo signal from the object; and after a lapse of a time interval, transmitting an ultrasound wave by at least one transducer included in the second transducer group to detect an echo signal from the object, the time interval is determined based on the object or the measurement result.

The method may further include determining a first movement speed, based on a characteristic of the object or the measurement result, wherein the detecting the echo signals may include: transmitting an ultrasound wave by at least one transducer included in the first transducer group at a first activation position and detect an echo signal from the object; and transmitting an ultrasound wave by at least one transducer included in the second transducer group at a second activation position, which has been spatially moved from the first activation position of the first transducer group at a first movement speed, and detect an echo signal from the object, and the first movement speed is determined based on a characteristic of the object or the measurement result.

The ultrasound waves transmitted into the object may include ultrasound plane waves.

The detecting the echo signals may include: while moving an ultrasound wave transmission position of a focus beam within each of the first transducer group and the second transducer group, transmitting the ultrasound waves of the focus beam onto the object by using the at least one transducer included in the first transducer group and the at least one transducer included in the second transducer group; and detecting the echo signals corresponding to the ultrasound wave transmission position of the focus beam.

The first movement speed may be determined based on the characteristic of the object which is at least one of a medical record and an examination position of the object.

The method may further include: correcting the first movement speed in response to a difference between the measured object change movement speed and the first movement speed being equal to or greater than a reference value; transmitting an ultrasound wave by at least one transducer included in a selected transducer group at a position which has been spatially moved from the first activation position at the corrected first movement speed, to detect an echo signal from the object; and measuring the object change movement speed from the detected echo signal, based on the corrected first movement speed.

The measuring the object change movement speed may include: calculating a variation image from two echo images which are sequentially captured; detecting a change position of the object from the variation image; and calculating the object change movement speed by using the change position of the object.

The method may further include: providing multiplexers that connect at least one selected transducer to a signal transfer channel, wherein the at least one transducer included in the first transducer group and the at least one transducer included in the second transducer group are selected transducers selected by the multiplexers.

The determining of the first movement speed may include measuring the object change movement speed by using the transducer array, and determining the first movement speed, based on the measurement result.

The method may further include transmitting the ultrasound waves onto the object to generate a shear wave in the object, wherein, the change in the object may include the shear wave, and the object change movement speed may be a propagation speed of the shear wave.

The generating the shear wave may include transmitting the ultrasound waves of a focus beam onto the object to generate the shear wave.

The generating the shear wave may include generating the shear wave at a plurality of points in the object.

The selecting the first transducer group and the second transducer group may include selecting the first transducer group, which is positioned at a first activation position at one end of the transducer array, and selecting the second transducer group which is positioned at a second activation position at an opposing end of the transducer array in a lengthwise direction. The detecting the echo signals may include transmitting the ultrasound waves by using transducers of a corresponding first or second transducer group at a position which has been alternately moved from the first activation position and the second activation position toward a center of the transducer array at a first movement speed, and detecting the echo signals from the object, and the first movement speed may be determined based on the object or the measurement result.

According to one or more exemplary embodiments, a probe includes: a transducer array that includes transducers; a controller configured to select a number of transducers to be activated in a first transducer group and a second transducer group, based on an object or a measurement result, transmit ultrasound waves onto the object by at least one transducer included in the first transducer group and at least one transducer included in the second transducer group, and detect echo signals from the object; and a communicator configured to transmit the echo signals to another electronic device.

According to one or more exemplary embodiments, there is provided a non-transitory computer-readable recording medium storing computer program codes which, when executed by a computer, cause the computer to execute a method of capturing an ultrasound image the method includes: selecting a number of transducers to be activated in a first transducer group and in a second transducer group, based on an object or a measurement result; transmitting ultrasound waves onto the object by at least one transducer, included in the first transducer group and at least one transducer included in the second transducer group, to detect echo signals from the object; and measuring an object change movement speed that is a speed at which a change in the object moves.

BRIEF DESCRIPTION OF THE DRAWINGS

The above and/or other aspects will become more apparent by describing certain exemplary embodiments, with reference to the accompanying drawings, in which.

DETAILED DESCRIPTION

Figure 1:
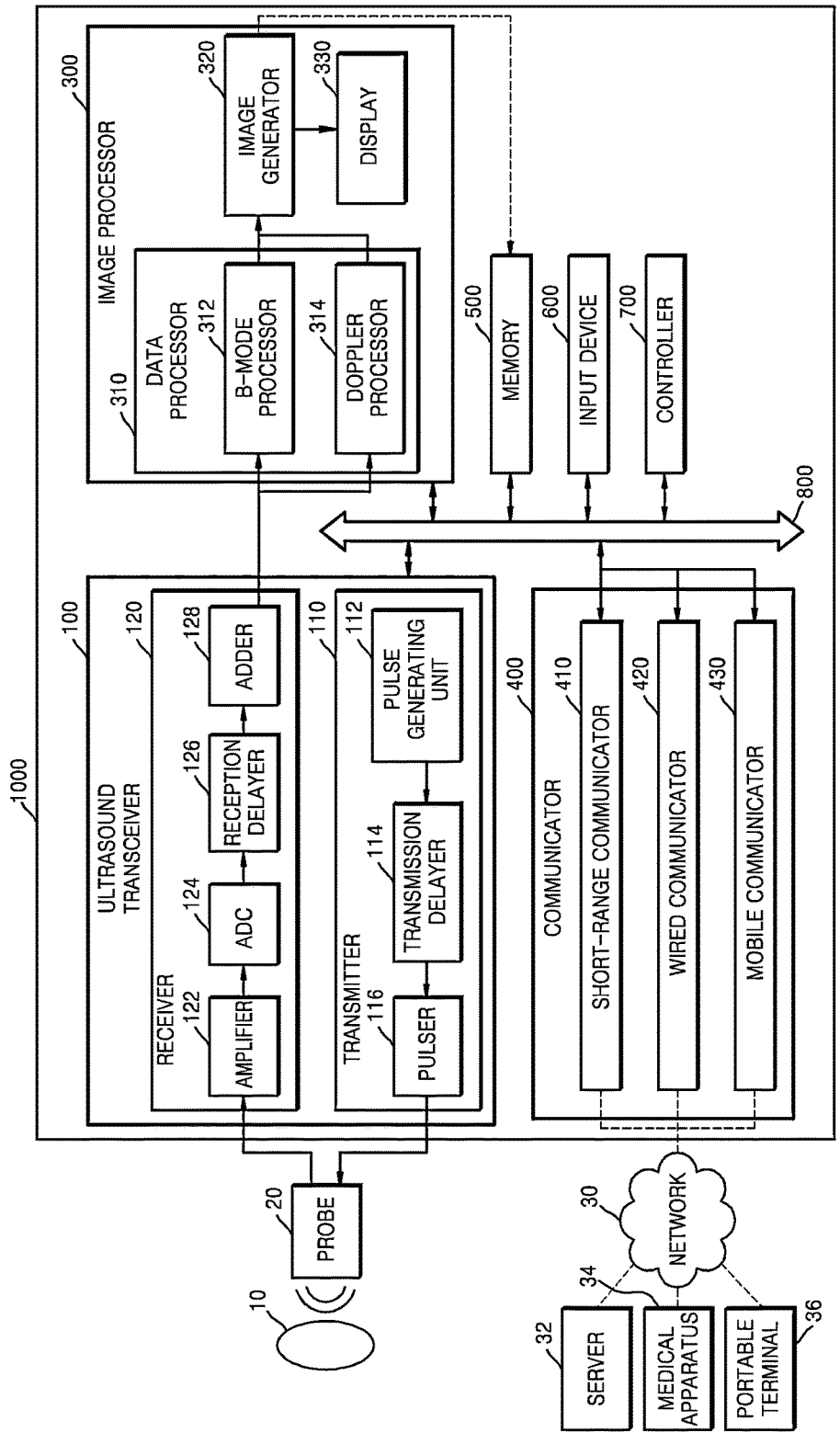
FIG. 1 is a block diagram illustrating a configuration of an ultrasound diagnostic apparatus according to an exemplary embodiment.

Certain exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

In the present specification, it should be understood that terms, such as 'including' or 'having', are intended to indicate the existence of the elements in the specification, and are not intended to preclude the possibility that one or more other elements may exist or may be added. Terms, such as 'unit' or 'module', should be understood as a unit that processes at least one function or operation and that may be embodied in a hardware manner, a software manner, or a combination of the hardware manner and the software manner.

The term "ultrasound image" used herein refers to an image of an object obtained by using an ultrasound wave. The term "object" used herein may include a human, an animal, or a body part of a human or an animal. For example, the object may include an organ such as the liver, heart, womb, brain, breast, or stomach, or a blood vessel. The "object" may be a phantom made of a material having a volume very similar to an effective atomic number and a density of a living creature and having properties similar to those of a human body.

The term "user" used herein may refer to, but is not limited to, a medical expert such as a doctor, a nurse, a clinical pathologist, a medical image expert, or an engineer who repairs a medical device.

FIG. 1 is a block diagram illustrating a configuration of an ultrasound diagnostic apparatus 1000 according to an exemplary embodiment. The ultrasound diagnostic apparatus 1000 may include one or more probes 20, an ultrasound transceiver 100, an image processor 300, a communicator 400, a memory 500, an input device 600, and a controller 700, which may be connected to one another via a bus 800.

The ultrasound diagnostic apparatus 1000 may be a cart-type ultrasound diagnostic apparatus or a portable ultrasound diagnostic apparatus. Examples of the portable ultrasound diagnostic apparatus may include, but are not limited to, a picture archiving and communication system (PACS) viewer, a smartphone, a laptop computer, a personal digital assistant (PDA), and a tablet personal computer (PC).

The probe 20 transmits an ultrasound signal to an object 10 according to a driving signal that is applied from the ultrasound transceiver 100 and receives an echo signal that is reflected from the object 10. The probe 20 includes a plurality of transducers that vibrate according to an electrical signal transmitted thereto and generate an ultrasound wave that is sound energy. The probe 20 may be connected in a wired or wireless manner to a main body of the ultrasound diagnostic apparatus 1000.

A transmitter 110 applies a driving signal to the probe 20. The transmitter 110 includes a pulse generator 112, a transmission delayer 114, and a pulser 116. The pulse generator 112 generates a pulse for forming a transmission ultrasound wave at a predetermined pulse repetition frequency (PRF), and the transmission delayer 114 applies a delay time for determining transmission directionality to the pulse. Each pulse to which the delay time is applied corresponds to each of a plurality of piezoelectric vibrators. The pulser 116 applies a driving signal (or a driving pulse) to the probe 20 at a timing corresponding to each pulse to which the delay time is applied.

A receiver 120 may generate ultrasound data by processing an echo signal received from the probe 20. The receiver 120 may include an amplifier 122, an analog to digital converter (ADC) 124, a reception delayer 126, and an adder 128. The amplifier 122 amplifies the echo signal for each channel, and the ADC 124 converts the amplified echo signal from an analog signal to a digital signal. The reception delayer 126 applies a delay time for determining a reception directionality to the echo signal that is digitized, and the adder 128 generates ultrasound data by summing the echo signal processed by the reception delayer 166. However, the amplifier 122 may be omitted. For example, when a sensitivity of the probe 20 is increased or the number of bits processed by the ADC 124 is increased, the amplifier 122 may be omitted.

The image processor 300 generates and displays an ultrasound image by performing scan conversion on the ultrasound data generated by the ultrasound transceiver 100. Examples of the ultrasound image may include a gray scale image obtained by scanning the object 10 in an amplitude (A) mode, a brightness (B) mode, and a motion (M) mode, and a Doppler image that shows the moving object 10 by using a Doppler effect. Examples of the Doppler image may include a blood flow Doppler image (also called a color Doppler image) showing the flow of blood, a tissue Doppler image showing a motion of tissue, and a spectral Doppler image showing a speed at which the object 10 moves, as a waveform.

A B-mode processor 312 extracts a B-mode component from the ultrasound data and processes the extracted B-mode component. An image generator 320 may generate an ultrasound image in which an intensity of a signal is represented as a brightness based on the B-mode component extracted by the B-mode processor 312.

Likewise, a Doppler processor 314 may extract a Doppler component from the ultrasound data, and the image generator 320 may generate a Doppler image in which a motion of the object 10 is represented as a color or a waveform based on the extracted Doppler component.

The image generator 320 may generate a three-dimensional (3D) ultrasound image by performing volume rendering on volume data, and may generate an elastic image that is obtained by imaging a degree of deformation of the object 10 according to pressure. The image generator 320 may represent various pieces of additional information as text or graphics to the ultrasound image. The generated ultrasound image may be stored in the memory 500.

The ultrasound diagnostic apparatus 1000 may include one or more displays 330 which display and output the generated ultrasound image. The display 330 may display and output on a screen through a graphical user interface (GUI) various pieces of information processed by the ultrasound diagnostic apparatus 1000 and the ultrasound image. The ultrasound diagnostic apparatus 1000 may include two or more display units 330 according to its type.

The communicator 400 is connected to a network 30 in a wired or wireless manner and communicates with an external device or a server. The communicator 400 may transmit and receive data with a server or other medical apparatuses in a hospital that are connected through a medical image information system such as a PACS. The communicator 400 may communicate data according to a digital imaging and communication in medicine (DICOM) standard.

The communicator 400 may transmit and/or receive data related to diagnosis of the object 10 such as an ultrasound image, ultrasound data, and Doppler data of the object 10 through the network 30, and may transmit and/or receive a medical image captured by another medical apparatus such as a computed tomography (CT) system, a magnetic resonance imaging (MRI) system, or an X-ray system. The communicator 400 may receive information about a patient's medical history or treatment schedule from the server and may use the information to diagnose the object 10. The communicator 400 may communicate data with a portable terminal of a doctor or the patient and/or with the server or the medical apparatus in the hospital.

The communicator 400 may be connected to the network 30 in a wired or wireless manner and may transmit or receive data with a server 32, a medical apparatus 34, or a portable terminal 36. The communicator 400 may include one or more elements that enable the communicator 400 to communicate with an external device, for example, a short-range communicator 410, a wired communicator 420, and a mobile communicator 430.

The short-range communicator 410 refers to a module for short-range communication within a predetermined distance. Examples of a short-range communication technology may include, but are not limited to, wireless LAN, Wi-Fi, Bluetooth, ZigBee, Wi-Fi Direct (WFD), ultrawide band (UWB), infrared data association (IrDA), Bluetooth low energy (BLE), and near field communication (NFC).

The wired communicator 420 refers to a module for communication using an electrical signal or an optical signal, and examples of a wired communication technology may include a paired cable, a coaxial cable, an optical fiber cable, and an Ethernet cable.

The mobile communicator 430 transmits and/or receives a wireless signal to and from at least one of a base station, an external terminal, and a server through a mobile communication network. Examples of the wireless signal may include various types of data such as a voice call signal, a video call signal, and a text and/or multimedia message.

The memory 500 stores various pieces of information processed by the ultrasound diagnostic apparatus 1000. For example, the memory 500 may store medical data related to diagnosis of the object 10 such as input/output ultrasound data or an ultrasound image, and may store an algorithm or a program performed in the ultrasound diagnostic apparatus 1000.

The memory 500 may be any of various types of storage media such as a flash memory, a hard disk, and an electrically erasable programmable read-only memory (EEPROM). The ultrasound diagnostic apparatus 1000 may operate web storage or a cloud server that performs a storage function of the memory 500 on the web.

The input device 600 may receive data for controlling the ultrasound diagnostic apparatus 1000 from a user. Examples of the input device 600 may include, but are not limited to, a keypad, a mouse, a touch panel, a touch screen, a track ball, and a jog switch. Examples of the input device 600 may further include an electrocardiogram measurement module, a respiration measurement module, a voice recognition sensor, a gesture recognition sensor, a fingerprint recognition sensor, an iris recognition sensor, a depth sensor, and a distance sensor.

The controller 700 controls an operation of the ultrasound diagnostic apparatus 1000. For example, the controller 700 may control an operation between the probe 20, the ultrasound transceiver 100, the image processor 300, the communicator 400, the memory 500, and the input device 600.

Although some or all of the probe 20, the ultrasound transceiver 100, the image processor 300, the communicator 400, the memory 500, the input device 600, and the controller 700 may be operated by a software module, the present exemplary embodiment is not limited thereto, and some of the elements may be operated by hardware. Also, at least some of the ultrasound transceiver 100, the image processor 300, and the communicator 400 may be included in the controller 700, but the present exemplary embodiment is not limited thereto.

Figure 2:
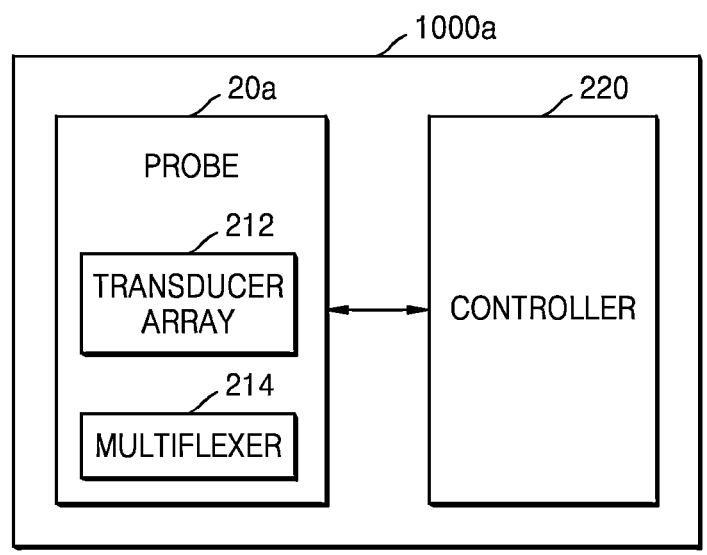
FIG. 2 is a block diagram illustrating a structure of an ultrasound diagnostic apparatus according to an exemplary embodiment.

FIG. 2 is a block diagram illustrating a structure of an ultrasound diagnostic apparatus 1000a according to an exemplary embodiment.

The ultrasound diagnostic apparatus 1000a according to the present exemplary embodiment includes a probe 20a and a controller 220.

The ultrasound diagnostic apparatus 1000a according to the present exemplary embodiment measures an object change movement speed that is a speed at which a change in an object is moved. The change of the object includes a wave which is propagated in the object and a movement of a target in the object.

The wave which is propagated in the object, for example, includes a shear wave, which is generated in an object tissue by the ultrasound diagnostic apparatus 1000a, and a pulsation based on a flow of blood. Since the wave is propagated in the object, a tissue of the object may be moved, and the ultrasound diagnostic apparatus 1000a may image a movement of the tissue of the object to measure propagation of the wave. A user may measure a propagation speed of the wave, infer a characteristic of the tissue of the object, and obtain information about a state of the tissue of the object.

A movement of the target in the object denotes that a portion of the object or a foreign material is moved in the object. For example, the movement of the target in the object may denote that a portion of the tissue of the object is moved through a blood vessel or a lymphatic vessel of the object, or through digestive organs such as an esophagus, a stomach, a small intestine, and a large intestine. As another example, the movement of the target in the object may denote that a foreign material is moved through a blood vessel or a lymphatic vessel of the object, or through digestive organs such as an esophagus, a stomach, a small intestine, and a large intestine.

The probe 20a transmits an ultrasound signal to an object 10 according to a driving signal, and receives an echo signal reflected from the object 10. The probe 20a includes a transducer array 212 that includes n transducers, where n is a natural number. The n transducers may be arranged in a one-dimensional (1D) array, a 1.5D array, or a two-dimensional (2D) array according to an exemplary embodiment. The probe 20a may include two or more transducer arrays.

The probe 20a according to an exemplary embodiment transmits an ultrasound wave by using at least one transducer included in a transducer group that is a range of an activated transducer among the n transducers, and receives an echo signal reflected from the object 10. For example, the probe 20a may transmit an ultrasound wave by using at least one transducer included in each of first and second transducer groups, and detect an echo signal from the object 10.

First, the probe 20a may transmit an ultrasound wave by using at least one transducer included in the first transducer group, e.g., a first activated transducer group, and detect an echo signal from the object 10. Subsequently, after a lapse of a time interval from a time when the ultrasound wave is transmitted by using the transducer included in the first transducer group, the probe 20a may transmit the ultrasound wave by using at least one transducer included in the second transducer group, e.g., a second activated transducer group, and detect an echo signal from the object 10. In this case, the time interval may be determined based on an object or a measurement result.

Alternatively, the probe 20a may transmit an ultrasound wave by using at least one transducer included in the first transducer group, and detect an echo signal from the object 10. The probe 20a may transmit an ultrasound wave by using at least one transducer included in the second transducer group at a position which has been moved from the first transducer group at a first movement speed, and detect an echo signal from the object 10. The first movement speed may be determined based on an object or a measurement result.

For example, the probe 20a may transmit an ultrasound wave by at least one transducer included in the first transducer group at a first activation position and detect an echo signal from the object. And the probe 20a may transmit an ultrasound wave by at least one transducer included in the second transducer group at a second activation position, which has been spatially moved from the first activation position of the first transducer group. Then, the probe 20a may detect an echo signal from the object. The first movement speed is determined based on a characteristic of the object or the measurement result.

The at least one transducer in the second transducer group may be the same transducer as used in the first transducer group or may be a transducer different from that used in the first transducer group. That is, the at least one transducer in the first transducer group and in the second transducer group may overlap or may be disposed not to overlap, i.e., the first transducer group and in the second transducer group may be disposed adjacent one another in a lengthwise direction of the transducer array.

The probe 20a according to an exemplary embodiment may transmit an ultrasound wave by using transducers of a plurality of transducer groups including m transducers among the n transducers, where m is a natural number less than n, and may receive an echo signal. The probe 20a may transmit an ultrasound wave by using a transducer group selected from a position which has been moved at the first movement speed, and receive an echo signal. The probe 20a may move a position of a selected transducer group at the first movement speed. In order to move the position of the selected transducer group, the controller 220 may output a control signal, which is used to select a transducer group at a position which has been moved at the first movement speed, to the probe 20a.

For example, a transducer being activated denotes that an ultrasound signal is transmitted by using a corresponding transducer, and an echo signal is detected. For example, only the m transducers among the n transducers of the transducer array 212 may be connected to a transmission/reception channel through which a signal is transmitted or received, and may be used to transmit an ultrasound wave and detect an echo signal. In this case, the m transducers connected to the transmission/reception channel are activated.

The controller 220 may select a range (i.e., a transducer group) of an activated transducer among the n transducers of the transducer array 212. The controller 220 may select a plurality of transducer groups, based on an object or a measurement result. For example, the controller 220 may select the first and second transducer groups. The controller 220 may select a transducer group so as to include a different number of transducers or the same number of transducers, based on an object or a measurement result.

In each transducer group period, the probe 20a may transmit an ultrasound wave onto an object, and detect an echo signal from the object. In this case, the probe 20a may transmit the ultrasound wave by using a transducer included in the transducer group selected by the controller 220, and detect the echo signal. Each transducer group period denotes a time period in which the probe 20a transmits an ultrasound wave by using a transducer, and receives an echo signal. The controller 220 may select a transducer group at a position which has been moved at the first movement speed. The probe 20a performs an operation which transmits an ultrasound wave by using an activated transducer and receives an echo signal in each transducer group period.

The controller 220 may determine the first movement speed, based on an object or a measurement result.

The first movement speed being determined based on an object denotes that the first movement speed is determined based on information which is previously stored based on the kind of an object. For example, an object may be classified into different kinds, based on a body tissue such as a bone, a muscle, a liver, a stomach, a heart, a brain, and a blood vessel, and the controller 220 may determine the first movement speed, based on information which is previously stored based on the kind of object being imaged.

The first movement speed being determined based on a measurement result denotes that a speed at which a change in an object is moved under a certain condition is measured in advance for determining the first movement speed, and the first movement speed is determined based on a measurement result. According to an exemplary embodiment, a speed is measured in a state where a position of a range of an activated transducer is fixed, or a speed is measured while moving a position of a range of a transducer which is activated at a certain speed.

When the first movement speed is determined, the controller 220 generates a control signal for selecting a transducer group at a moved position, based on the first movement speed, and outputs the control signal to the probe 20a. For example, the controller 220 may control a multiplexer (214) connected between the probe 20a and the transmission/reception channel to move a position of a selected transducer group at the first movement speed.

The controller 220 may generate an echo image from an echo signal which is acquired by using a selected transducer group at different positions, and measure an object change movement speed, which is a speed at which a change in an object is moved, from the echo image. The object change movement speed is a distance by which the change in the object moves per hour. A movement distance of the change in the object may be calculated by measuring a position of the change in the object from the echo signal or the echo image. For example, when a shear wave is propagated in the object, the controller 220 may detect a position of a movement of a tissue, which is caused by the shear wave, to measure the position of the change in the object.

The controller 220 may change the number of transducers included in a transducer group, based on the object change movement speed, and select transducer groups including a changed number of transducers. For example, when the object change movement speed becomes relatively high, the controller 220 may select transducer groups including a greater number of transducers. Alternatively, when the object change movement speed becomes relatively low, the controller 220 may select transducer groups including a smaller number of transducers.

For example, in order to detect a change in an object that occurs at a high speed, the ultrasound diagnostic apparatus 1000a may transmit an ultrasound wave onto a relatively wide internal region of the object, and detect an echo signal. In order to detect the echo signal for the wide internal region of the object, the ultrasound diagnostic apparatus 1000a may select transducer groups including a greater number of transducers, transmit an ultrasound wave by using transducers included in the selected transducer groups, and detect an echo signal. On the other hand, in order to detect a change in an object that occurs at a relatively low speed, the ultrasound diagnostic apparatus 1000a may transmit an ultrasound wave onto a relatively narrow internal region of the object, and detect an echo signal. In order to detect the echo signal for the narrow internal region of the object, the ultrasound diagnostic apparatus 1000a may select transducer groups including a small number of transducers, transmit an ultrasound wave by using transducers included in the selected transducer groups, and detect an echo signal.

Figure 3:
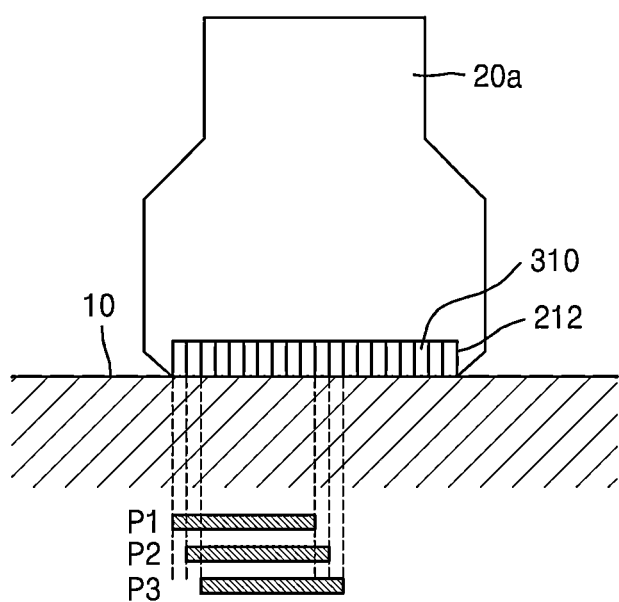
FIG. 3 is a diagram illustrating a probe according to an exemplary embodiment.

FIG. 3 is a diagram illustrating the probe 20a according to an exemplary embodiment.

The probe 20a contacts a surface of the object 10, emits an ultrasound wave to the object 10, and detects an echo signal. The probe 20a includes a transducer array 212 including a plurality of transducers 310. Each of the transducers 310 includes a piezoelectric element, generates an ultrasound wave from an electrical signal, and detects an ultrasound wave. The transducer array 212 may be, for example, a 1D array, a 2D array, or a 3D array.

The ultrasound diagnostic apparatus 1000a may include transmitting ends and receiving ends, the number of which is less than the number of transducers 310. Each of the transmitting ends may include a pulse generator, a transmission delayer, and a pulser, and each of the receiving ends may include an amplifier, an ADC, a reception delayer, and an adder. The transmitting end may be provided in the probe 20a or the ultrasound transceiver 100.

The transmitting end and the receiving end may be connected to the transducer 310 through a multiplexer. For example, when 256 transducers 310 are provided in the probe 20a and 128 transmitting and receiving ends are provided in the ultrasound diagnostic apparatus 1000a, two transducers 310 may be connected to one multiplexer, and each multiplexer may be connected to one transmitting end and one receiving end. In this case, a first transducer 310 and a 129th transducer 310 may be connected to a first multiplexer, and a second transducer 310 and a 130th transducer 310 may be connected to a second multiplexer. The controller 220 outputs a selection signal to each multiplexer, and determines a transducer 310 to be connected to a transmitting end and a receiving end. Only a selected transducer 310 among the plurality of transducers 310 connected to the multiplexers is connected to a transmitting end or a receiving end and is activated.

According to another exemplary embodiment, the ultrasound diagnostic apparatus 1000a may include transmitting ends and receiving ends, the number of which is equal to the number of transducers 310, and may store or transmit only data output from a receiving end connected to an activated transducer 310.

The ultrasound diagnostic apparatus 1000a according to exemplary embodiments activates only some transducers 310 among the plurality of transducers 310 of the ultrasound diagnostic apparatus 200 during ultrasound wave transmission/reception, transmits an ultrasound wave by changing a range of activated transducers 310, and detects an echo signal. The expression 'range of activated transducers' used herein is referred to as a transducer group. When a transducer group is moved, it means that a range of activated transducers 310 is changed, and the transducers of different positions are selected to be activated. For example, first to tenth transducers may be activated during a period P1, second to eleventh transducers may be activated during a period P2, and third to twelfth transducers may be activated during a period P3. During each of the periods P1 to P3, an operation which transmits an ultrasound wave by using activated transducers and detects an echo signal may be performed.

A time interval between the period P1, the period P2, and the period P3 may be determined based on a minimum time which is needed for transmitting an ultrasound wave to detect an echo signal. For example, the time interval between the period P1, the period P2, and the period P3 may be determined to be longer than the minimum time which is needed for transmitting the ultrasound wave to detect the echo signal.

An interval between transducers 310 activated for the period P1, the period P2, and the period P3 may be determined based on the first movement speed. For example, when the first movement speed has a first value, the first to tenth transducers may be activated during the period P1, the second to eleventh transducers may be activated during the period P2, and the third to twelfth transducers may be activated during the period P3. As another example, when the first movement speed has a second value that is twice as great as the first value, the first to tenth transducers may be activated during the period P1, the third to twelfth transducers may be activated during the period P2, and the fifth to fourteenth transducers may be activated during the period P3. I.e., the distance between the positions of a start transducer of the transducers activated in each period P1, P2, and P3 becomes greater as the first movement speed becomes greater.

Figure 4:
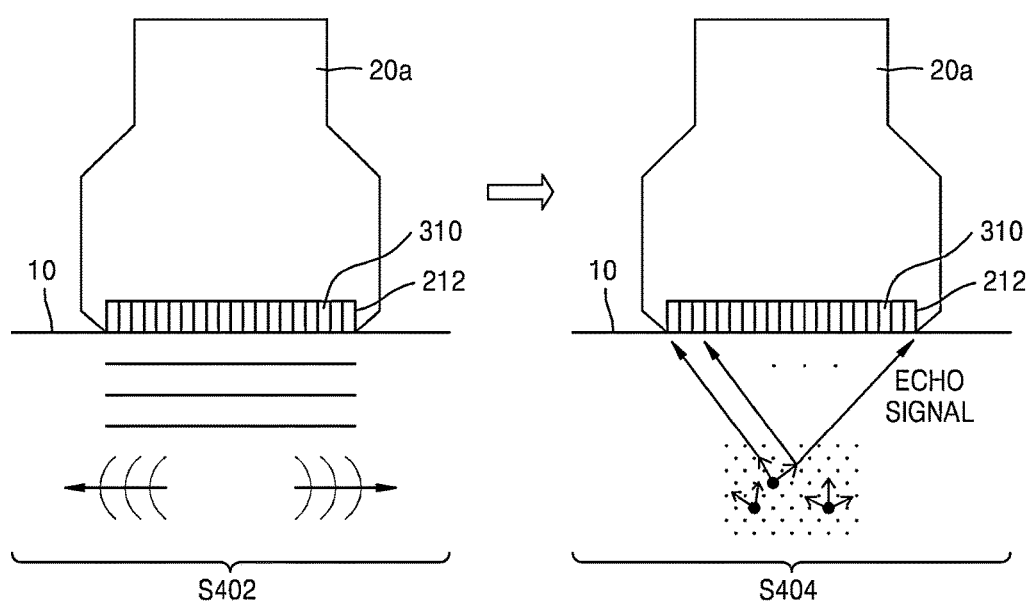
FIG. 4 is a diagram for describing an operation of detecting a change in an object.

FIG. 4 is a diagram for describing an operation of detecting a change in an object.

When a change in the object 10 occurs, the ultrasound diagnostic apparatus 1000a emits an ultrasound wave to the object 10 (operation S402), detects an echo signal corresponding to the ultrasound wave (operation S404), and obtains an image of the object 10. For example, in measuring a shear wave which is propagated in an object, since the shear wave propagates at a high speed, for example, of a maximum of 10 m per second, an ultrasound echo image is acquired and stored at a high frequency of about 5,000 Hz. The ultrasound diagnostic apparatus 1000a images a variation of tissue of the object 10 at a high speed by using the transducer array 212 of the probe 20a. The ultrasound diagnostic apparatus 1000a may obtain a B mode image.

The controller 220 calculates a variation image from two echo images that are continuously captured, detects a point at which the variation of the tissue occurs, and calculates a speed at which the variation moves. For example, in order to measure a shear wave propagation speed, a variation of tissue that is formed by the shear wave needs to be accurately calculated. The controller 220 detects the variation of the tissue by comparing two echo images that are continuously captured and calculating a degree of change in scattering.

The variation of the object 10 may be calculated by using cross-correlation. For example, the variation image may be calculated by performing cross-correlation on two echo images that are continuously captured.

According to another exemplary embodiment, the variation image may be calculated as a difference image between two echo images that are continuously captured.

The variation calculated in all of the pixels is stored as the variation image. For example, the controller 220 calculates the speed of the shear wave in all of the pixels of the image by calculating a propagation speed of a wave front of the shear wave in a variation map. In capturing the echo image, the probe 20a according to an exemplary embodiment moves a transducer group of the transducers 310 of the transducer array 212 at a predicted shear wave propagation speed. As described above, the ultrasound diagnostic apparatus 1000a includes transmitting ends and receiving ends, the number of which is less than the number of transducers 310, and activates only the transducers 310 included in the transducer group during ultrasound wave transmission/reception. The probe 20a may increase a degree of accuracy in measuring the shear wave propagation speed by moving the transducer group of the transducers 310 at the predicted shear wave propagation speed and obtaining an echo image of a variation of tissue in a wider region.

Figure 5:
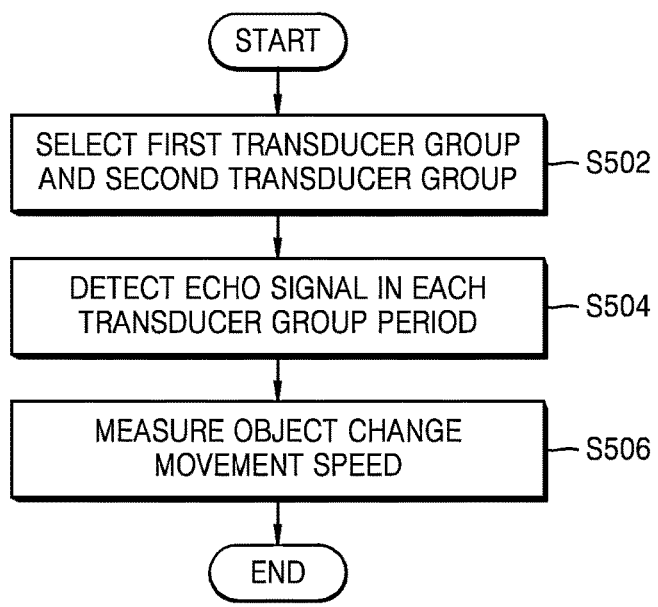
FIG. 5 is a flowchart illustrating an ultrasound image capturing method according to an exemplary embodiment.

FIG. 5 is a flowchart illustrating an ultrasound image capturing method according to an exemplary embodiment.

The ultrasound image capturing method according to the present exemplary embodiment may be performed by the ultrasound diagnostic apparatus 1000a of FIG. 2. An ultrasound image capturing method according to exemplary embodiments may be performed by various ultrasound diagnostic apparatuses in addition to the ultrasound diagnostic apparatus 1000a of FIG. 2.

In operation S502, the ultrasound diagnostic apparatus 1000a selects a first transducer group and a second transducer group that are ranges of activated transducers among n transducers of a transducer array, based on an object or a measurement result.

In selecting a plurality of transducer groups based on an object or a measurement result, the ultrasound diagnostic apparatus 1000a may select each transducer group to include a different number of transducers or the same number of transducers.

The ultrasound diagnostic apparatus 1000a may further determine a time interval or a first movement speed, based on a characteristic of an object or a measurement result. For example, the first movement speed may be determined based on at least one of a medical record and an examination position of an object. The ultrasound diagnostic apparatus 1000a may determine the first movement speed depending on the kind of an object, or may measure an object change movement speed in advance and determine the first movement speed, based on a measurement result. For example, the ultrasound diagnostic apparatus 1000a may determine the measured object change movement speed as the first movement speed.

Subsequently, in operation S504, the ultrasound diagnostic apparatus 1000a may detect an echo signal in each transducer group period. The ultrasound diagnostic apparatus 1000a may transmit an ultrasound wave onto an object by using at least one transducer included in each of the first and second transducer groups, and detect an echo signal from the object.

For example, the ultrasound diagnostic apparatus 1000a may transmit an ultrasound wave by using at least one transducer included in the first transducer group, and detect an echo signal from an object. After a lapse of a time interval from a time when the ultrasound wave is transmitted by using the transducer included in the first transducer group, the ultrasound diagnostic apparatus 1000a may transmit an ultrasound wave by using at least one transducer included in the second transducer group, and detect an echo signal from the object.

As another example, the ultrasound diagnostic apparatus 1000a may move a position of a selected transducer group at the first movement speed. For example, a range of a transducer connected to a transmitting end and a receiving end for a signal may be moved at the first movement speed. The ultrasound diagnostic apparatus 1000a may transmit an ultrasound wave by using at least one transducer included in the first transducer group, and detect an echo signal from an object. The ultrasound diagnostic apparatus 1000a may transmit an ultrasound wave by using the second transducer group at a position which has been moved from the first transducer group at the first movement speed, and detect an echo signal from the object.

The ultrasound diagnostic apparatus 1000a may detect an echo signal by using at least one transducer included in a selected transducer group at a position which has been moved at the first movement speed. At least one transducer included in a transducer group transmits an ultrasound wave and detects an echo signal during a transducer group period.

The ultrasound diagnostic apparatus 1000a may emit different types of ultrasound signals in respective transducer group periods. For example, the ultrasound diagnostic apparatus 1000a may transmit an unfocused beam by using at least one transducer included in the first transducer group, and may transmit a focused beam by using at least one transducer included in the second transducer group. The ultrasound diagnostic apparatus 1000a may determine what type of ultrasound signal is emitted during each transducer group period.

In operation S506, the ultrasound diagnostic apparatus 1000a measures an object change movement speed from the echo signal. For example, the ultrasound diagnostic apparatus 1000a generates an echo image from the echo signal, and calculates a change speed of the object by using echo images which are captured in the respective transducer group periods.

Figure 6:
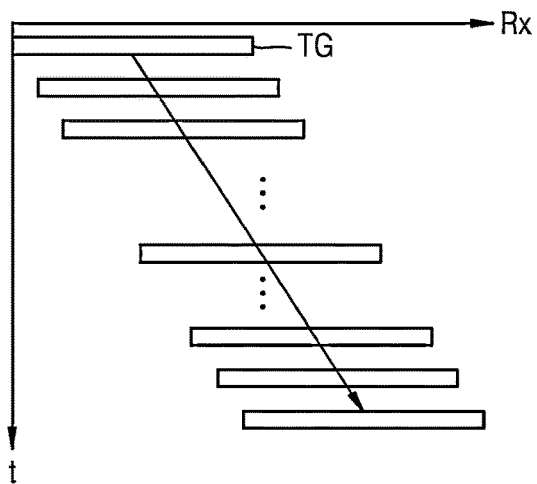
FIG. 6 is a diagram showing a transducer group selected at a position which is moved, according to an exemplary embodiment.

FIG. 6 is a diagram showing a transducer group selected at a position which is moved, according to an exemplary embodiment.

As illustrated in FIG. 6, the probe 20a moves a position of a selected transducer group (TG) at the first movement speed. For example, when 256 transducers are included in the probe 20a, first to 128th transducers 310 may be activated during a first transducer group period, and second to 129th transducers 310 may be activated during a second transducer group period. For example, when the first movement speed is faster than the above-described example, the first to 128th transducers 310 may be activated during the first transducer group period, and the third to 130th transducers 310 may be activated during the second transducer group period.

Figure 7:
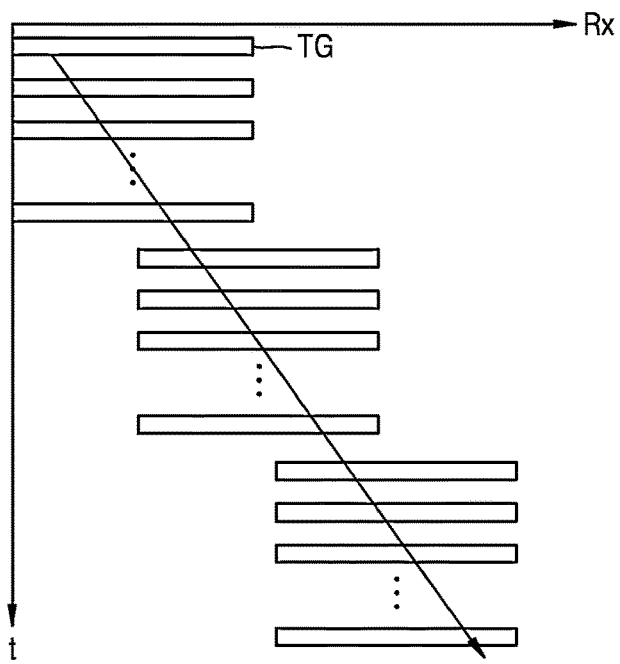
FIG. 7 is a diagram showing a transducer group selected at a position which is moved, according to an exemplary embodiment.

FIG. 7 is a diagram showing a transducer group selected at a position which is moved, according to an exemplary embodiment.

As illustrated in FIG. 7, when a position of a selected transducer group (TG) is moved at the first movement speed, the probe 20a may activate at least one transducer of the same transducer group (TG) through "a"-time repetition, and then may activate at least one transducer of a transducer group (TG) at a moved position through "a"-time repetition. For example, first to 128th transducers 310 may be activated during first to tenth transducer group periods, and tenth to 138th transducers 310 may be activated during eleventh to twentieth transducer group periods. According to the present exemplary embodiment, a load caused by a movement of the position of the transducer group (TG) is reduced.

In FIGS. 6 and 7, a case in which a transducer group is selected at a position which has been moved in one direction has been described as an example. However, an exemplary embodiment is not limited thereto, and a transducer group including a varying number of transducers may be selected at various positions of a transducer array, based on an object or a measurement result.

In FIGS. 6 and 7, a case of selecting transducer groups including the same number (i.e., 128) of transducers is illustrated. However, according to another exemplary embodiment, the ultrasound diagnostic apparatus 1000a may select a plurality of transducer groups including a different number of transducers, based on an object or a measurement result.

For example, the ultrasound diagnostic apparatus 1000a may select a transducer group including a number of transducers which is increased according to a movement of a change in an object. When 256 transducers are included in the probe 20a, first to 128th transducers may be activated during a first transducer group period, and then, first to 130th transducers may be activated during a second transducer group period. First to 256th transducers may be activated during a 64th transducer group period.

According to another embodiment, the ultrasound diagnostic apparatus 1000a may select a plurality of transducer groups including a different number of transducers at a moved position, based on an object or a measurement result.

For example, since a change in an object is moved, the ultrasound diagnostic apparatus 1000a may select a transducer group including an increased number of transducers at a moved position. When 256 transducers are included in the probe 20a, first to 128th transducers may be activated during a first transducer group period, and then, second to 130th transducers may be activated during a second transducer group period. 64th to 256th transducers may be activated during a 64th transducer group period.

According to another exemplary embodiment, the ultrasound diagnostic apparatus 1000a may select a plurality of transducer groups at an irregular position, based on an object or a measurement result.

For example, since a change in an object is moved, the ultrasound diagnostic apparatus 1000a may select a transducer group at an irregularly moved position. When 256 transducers are included in the probe 20a, first to 128th transducers may be activated during a first transducer group period, second to 129th transducers may be activated during a second transducer group period, 128th to 255th transducers may be activated during a third transducer group period, and 129th to 256th transducers may be activated during a fourth transducer group period. I.e., a start position of the transducer activated group may be moved at an irregular interval or distance.

Figure 8:
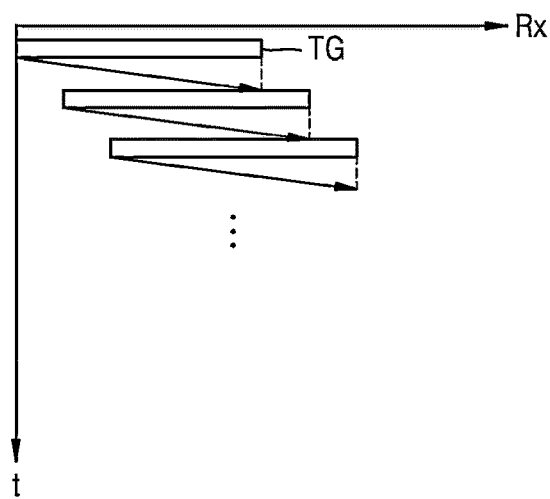
FIG. 8 is a diagram for describing an operation of obtaining an echo image within each transducer group (TG), according to an exemplary embodiment.
Figure 9:
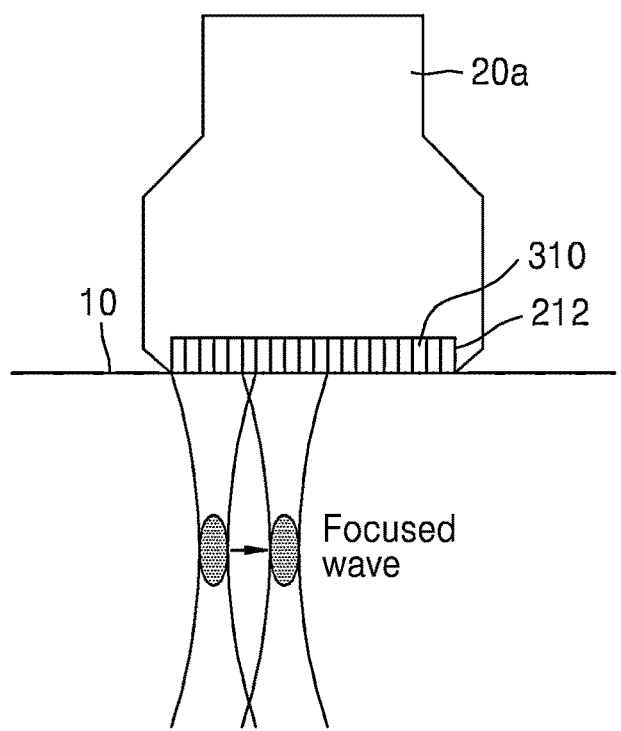
FIG. 9 is a diagram for describing an operation of obtaining an echo image within each transducer group (TG), according to an exemplary embodiment.

FIG. 8 is a diagram for describing an operation of obtaining an echo image within each transducer group (TG), according to an exemplary embodiment. FIG. 9 is a diagram for describing an operation of obtaining an echo image within each transducer group (TG), according to an exemplary embodiment.

A multi-beam method transmits an ultrasound wave onto an object 10 by using a plurality of transducers. The multi-beam method includes a plane wave method and a focus beam method. The plane wave method is a method that simultaneously emits an ultrasound wave from a plurality of transducers. The focus beam method is a method in which emitted ultrasound waves focus on a certain point because there is a time difference between a plurality of transducers which transmit the ultrasound wave. In the focus beam method, a degree of focusing may be changed according to exemplary embodiments. For example, since a time difference between a plurality of transducers is slight, a focus beam which is output similar to a plane wave may be generated, or an ultrasound wave may be output by generating a focus beam in order for the ultrasound wave to focus on a narrow region. As an ultrasound wave focuses on a narrow region, an energy level per unit area increases. A size of a focusing region of a focus beam may be changed according to exemplary embodiments. A plane wave or a focus beam similar to the plane wave may be referred to as an unfocused beam. The plane wave may be referred to as a parallel beam.

According to an exemplary embodiment, when an echo image is obtained in each transducer group (TG), a scan method using an ultrasound wave of a focus beam may be used. As illustrated in FIG. 8, according to the present exemplary embodiment, the probe 20a may scan an object by using a focus beam which is transmitted from at least one transducer included in each transducer group (TG). When a scan operation using at least one transducer included in a certain transducer group ends, the probe 20a may perform the scan operation by using at least one transducer included in another transducer group. The probe 20a, as illustrated in FIG. 9, may detect an echo signal while scanning the object 10 by using a focus beam which is transmitted from at least one transducer included in a transducer group.

A position of a transducer group may be moved at the first movement speed. A scan operation using at least one transducer included in each transducer group ends within a certain time interval. For example, a scan operation using each transducer group may be performed at a maximum speed supported by the ultrasound diagnostic apparatus 1000a.

Figure 10:
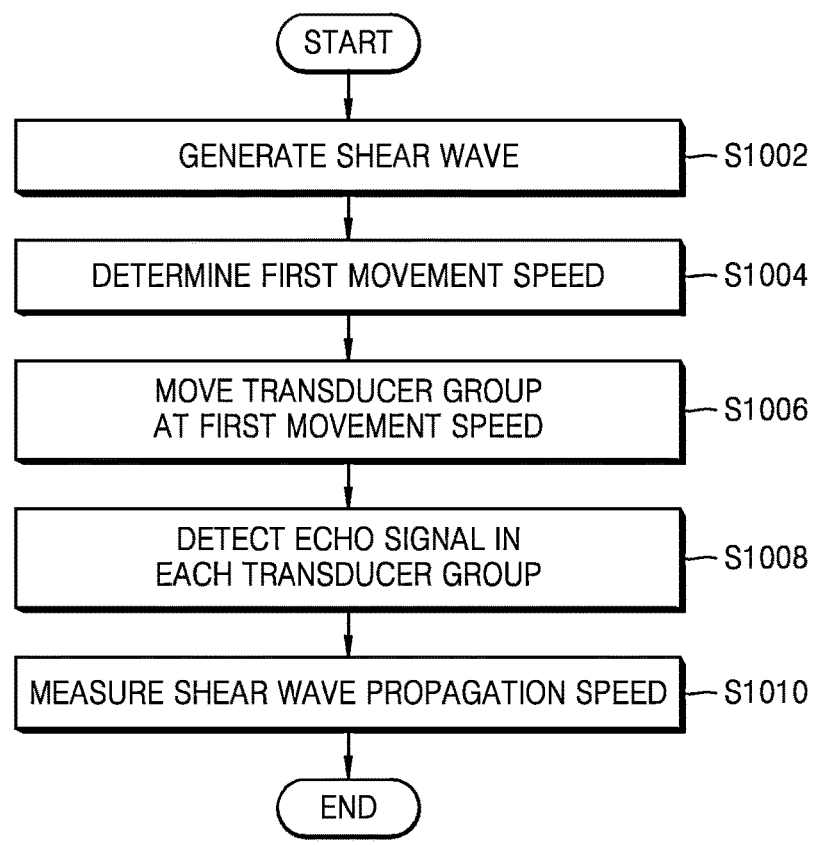
FIG. 10 is a flowchart illustrating an ultrasound image capturing method according to an exemplary embodiment.

FIG. 10 is a flowchart illustrating an ultrasound image capturing method according to an exemplary embodiment.

In operation S1002, the ultrasound diagnostic apparatus 1000a transmits an ultrasound wave of a focus beam onto the object 10 by using the probe 20a to generate a shear wave, i.e., a secondary wave, in a tissue of the object 10.

Figure 11:
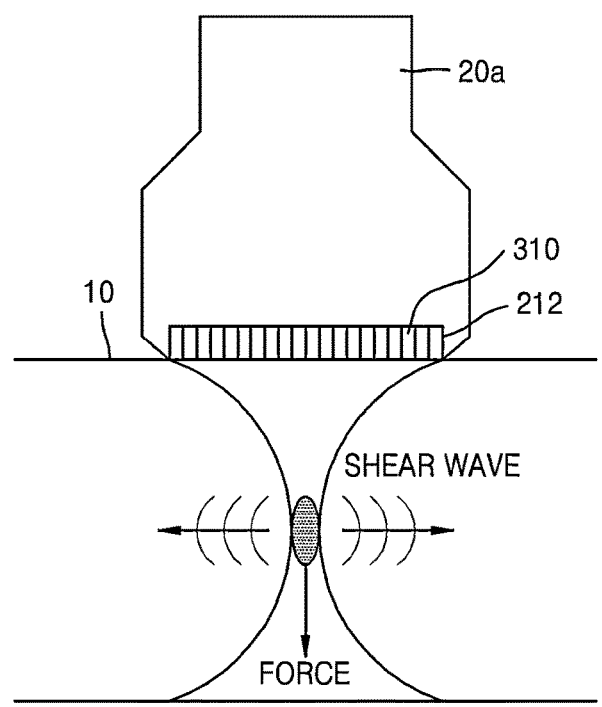
FIG. 11 is a diagram for describing an operation of generating a shear wave in an object, according to an exemplary embodiment.
Figure 12:
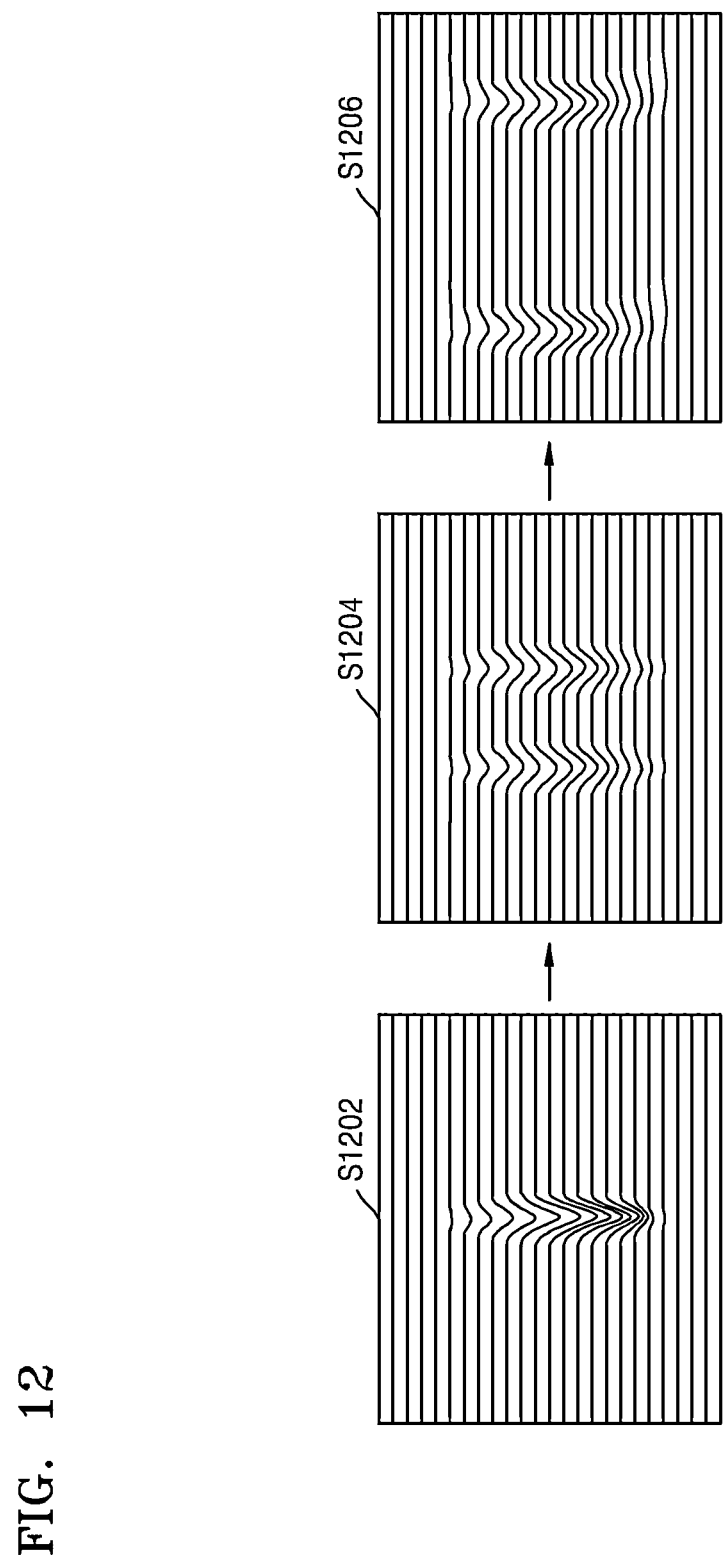
FIG. 12 is a diagram for describing propagation of a shear wave.

FIG. 11 is a diagram for describing an operation of generating a shear wave in the object 10, according to an exemplary embodiment. FIG. 12 is a diagram for describing propagation of a shear wave.

As illustrated in FIG. 11, when an ultrasound wave of a focus beam is transmitted onto the object 10, a depth-direction force is applied to the object 10. When the depth-direction force is generated, as illustrated in FIG. 12, a tissue of the object 10 moves in a depth direction from a point at which the force is generated in operation S1202, and a movement aspect moves in a horizontal direction vertical to the depth direction, i.e., a substantially perpendicular direction to a direction of the primary ultrasound wave, in operations S1204 and S1206. A movement aspect of a tissue being moved in the horizontal direction is referred to as a shear wave.

Elastography for measuring a stiffness of an object tissue with an ultrasound wave may be used for an initial diagnosis of various cancers. Such a cancer diagnostic method is a method that measures a rigidity degree of a tissue to determine the presence of cancer, based on a fact that the cancerous tissue is more rigid than normal tissue. Shear wave elastic technology, which generates a shear wave and measures a propagation speed of the shear wave to measure a shear elastic modulus, quantitatively displays a stiffness of a tissue. The present exemplary embodiment provides an ultrasound diagnostic apparatus and an ultrasound image capturing method, which measure propagation of a shear wave at a high speed by using the shear wave elastic technology.

The ultrasound diagnostic apparatus 1000a may measure a propagation speed of a shear wave to measure a shear elastic modulus of an object, and may quantitatively display a stiffness of a tissue from the shear elastic modulus. The shear elastic modulus is calculated by multiplying the square of a shear wave speed by a density of a medium. The probe 20a transmits an ultrasound wave of a focus beam onto a target point to generate a shear wave in the object 10. The target point may be a portion of a body tissue such as a liver, a kidney, or a muscle.

In operation S1004, the ultrasound diagnostic apparatus 1000a determines the first movement speed, based on an object or a measurement result. The order of an operation S1002 and an operation S1004 may be changed according to exemplary embodiments, and the operation S1002 and the operation S1004 may be performed in parallel.

The ultrasound diagnostic apparatus 1000a moves a transducer group (TG) at the first movement speed in operation S1006, and transmits an ultrasound wave in each transducer group to detect an echo signal in operation S1008. The ultrasound diagnostic apparatus 1000a according to an exemplary embodiment may move a transducer group (TG) at the first movement speed in each transducer group period. For example, the ultrasound diagnostic apparatus 1000a may select the transducer group to include a transducer corresponding to a position which has been moved at the first movement speed. The ultrasound diagnostic apparatus 1000a according to another exemplary embodiment may transmit an ultrasound wave during an "a"-time transducer group period by using the same transducer group, and then repeat, "a" times, an operation of transmitting an ultrasound wave by using a transducer group at a moved position.

The ultrasound diagnostic apparatus 1000a measures a shear wave propagation speed as an object change speed from the echo signal in operation S1010. For example, the ultrasound diagnostic apparatus 1000a generates an echo image from the echo signal, calculates a variation image from the echo image, determines a position of a shear wave in an image by using the variation image, and measures a propagation speed of a shear wave in operation S1010. According to an exemplary embodiment, the variation image may be calculated as a difference image between two continuous echo images. According to another exemplary embodiment, the variation image may be calculated as an image in which two continuous echo images cross-correlate with each other.

Figure 13:
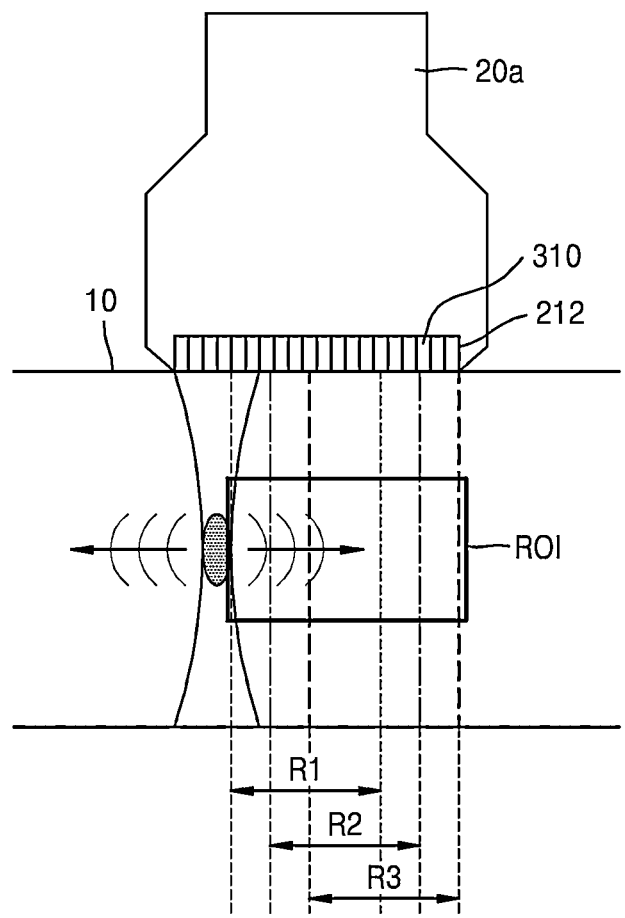
FIG. 13 is a diagram for describing an operation of imaging a variation of a tissue, according to an exemplary embodiment.

FIG. 13 is a diagram for describing an operation of imaging a variation of a tissue, according to an exemplary embodiment.

When a variation of tissue occurs, the probe 20a may move a transducer group of the transducers 310 within a range of a region of interest (ROI) at the first movement speed. As a time changes to t1, t2, and t3, the transducer group of the transducers 310 is moved to correspond to regions R1, R2, and R3.

Figures 14, 15:
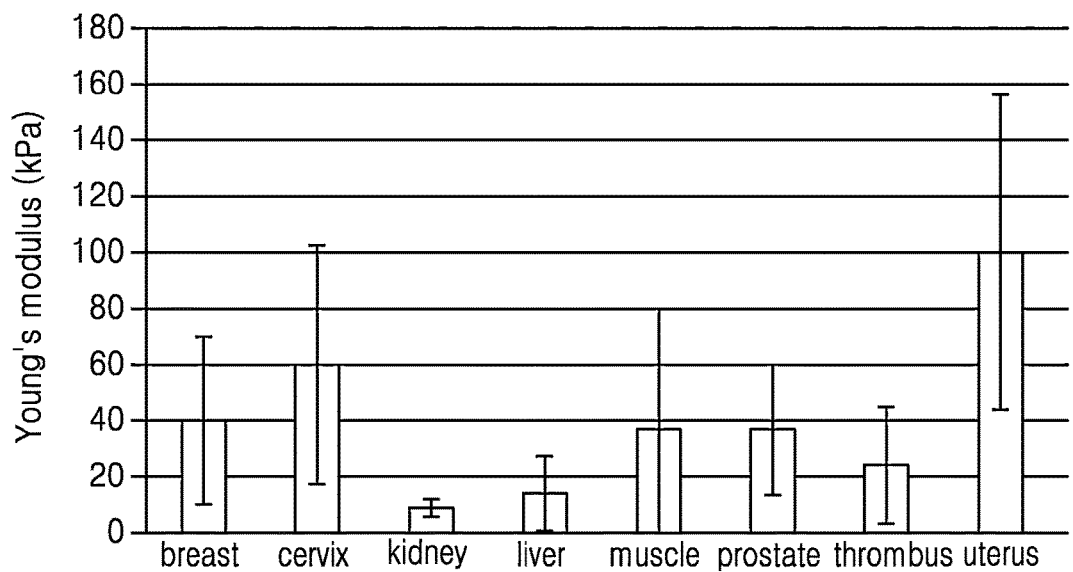
FIG. 14 is a diagram for describing an operation of calculating a first movement speed when measuring a shear wave propagation speed, according to an exemplary embodiment.
FIG. 15 is a diagram for describing an operation of calculating a first movement speed, according to an exemplary embodiment.

FIG. 14 is a diagram for describing an operation of calculating a first movement speed when measuring a shear wave propagation speed, according to an exemplary embodiment.

According to an exemplary embodiment, in measuring a shear wave propagation speed, the ultrasound diagnostic apparatus 1000a may calculate the first movement speed by using pre-stored data, based on a target point. For example, as shown in FIG. 14, a Young's modulus and a density for each organ of a body may be previously stored. The Young's modulus and the density may be stored in, for example, the memory 500 (see FIG. 1). The first movement speed Cs may be calculated by using the Young's modulus, the density of each organ, and Equation (1):

$$C_s = \sqrt{\frac{E}{3\rho}} \quad (1)$$

where E is the Young's modulus and p is the density.

FIG. 15 is a diagram for describing an operation of calculating a first movement speed, according to an exemplary embodiment.

According to an exemplary embodiment, the first movement speed may be determined based on the kind of object and identification information of the object. In diagnosing a patient with the ultrasound diagnostic apparatus 1000a, a characteristic of a tissue may be changed based on a personal characteristic of the patient or a progress of a disease of the patient. According to the present exemplary embodiment, the ultrasound diagnostic apparatus 1000a calculates the first movement speed, based on an imaging area and identification information A and B indicating who the object is. Information (for example, a Young's modulus and a density) for calculating the first movement speed or information about the first movement speed may be stored in the ultrasound diagnostic apparatus 1000a, or the ultrasound diagnostic apparatus 1000a may acquire the information from a server.

Figure 16:
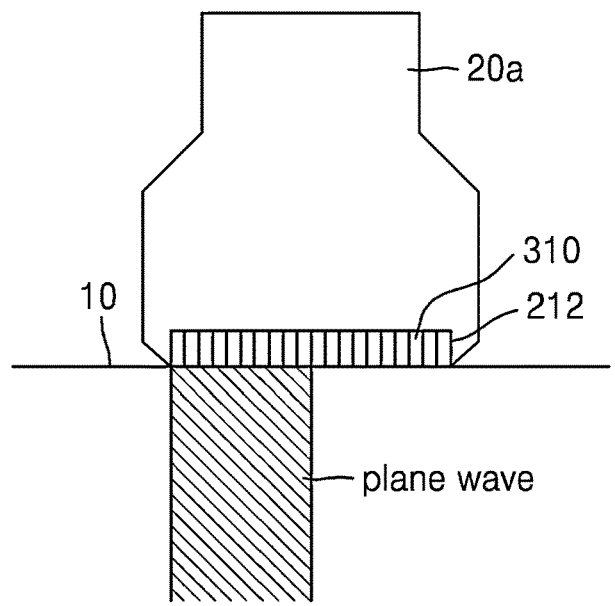
FIG. 16 is a diagram for describing an operation of obtaining an echo image within each transducer group (TG), according to an exemplary embodiment.

FIG. 16 is a diagram for describing an operation of obtaining an echo image within each transducer group (TG), according to an exemplary embodiment.

According to an exemplary embodiment, when transmitting an ultrasound wave to obtain an echo image in each transducer group (TG), an ultrasound plane wave is transmitted. Since a shear wave has a relatively fast propagation speed, the probe 20a may perform imaging while moving each transducer group (TG) at a relatively fast speed. By using the plane wave method, an imaging time in each transducer group (TG) is greatly shortened, and thus, an object is imaged at a high speed. In the plane wave method, the transducers 310 of a certain transducer group (TG) simultaneously transmit an ultrasound wave, and after a certain time elapses, the transducers 310 of the certain transducer group (TG) detect an echo signal.

Figure 17:
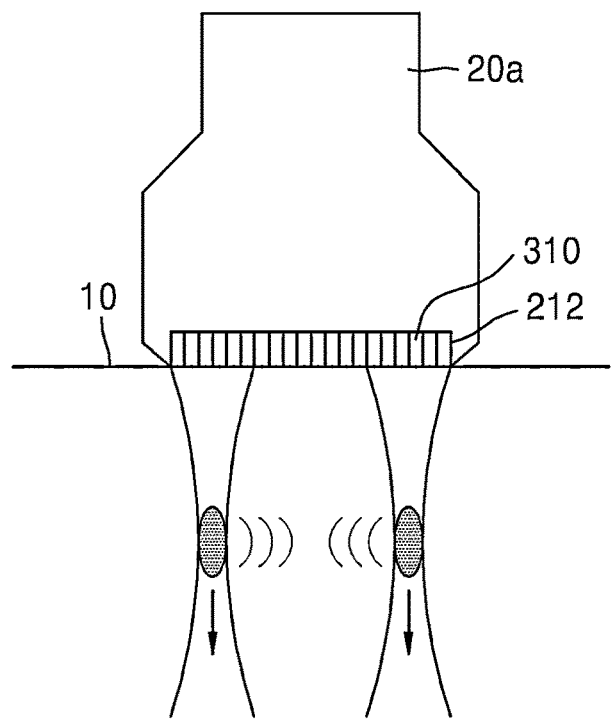
FIG. 17 is a diagram for describing an operation of generating a shear wave, according to an exemplary embodiment.

FIG. 17 is a diagram for describing an operation of generating a shear wave, according to an exemplary embodiment.

According to the present exemplary embodiment, the ultrasound diagnostic apparatus 1000a may generate a shear wave at a plurality of points. For example, as illustrated in FIG. 17, the probe 20a may simultaneously transmit, onto an object, focus beams which are used to generate a shear wave at both ends, and generate the shear wave at positions corresponding to the both ends of the probe 20a. Since a magnitude of a shear wave is attenuated by propagation of the shear wave, when the shear wave is generated and measured at a plurality of points, a shear wave having high amplitude is measured within a short time, and thus, an accuracy of measurement of a shear wave and a signal-to-noise ratio (SNR) are enhanced.

In order to measure a shear wave which is generated at a plurality of points, the probe 20a may select a transducer group at positions which are moved in a plurality of directions.

The ultrasound diagnostic apparatus 1000a may select a first transducer group which is positioned at one end of a transducer array, and select a second transducer group which is positioned at another, opposing end of the transducer array, in a lengthwise direction.

The probe 20a may transmit an ultrasound wave by using a transducer group at a position which has been alternately moved from the first transducer group and the second transducer group toward a center of the transducer array at the first movement speed, and detect an echo signal from an object. The probe 20a may transmit an ultrasound wave by alternately using transducer groups at a position, which has been moved from the first transducer group toward the center of the transducer array at the first movement speed, and transducer groups at a position which has been moved from the second transducer group toward the center of the transducer array at the first movement speed.

For example, the probe 20a may select the first transducer group, which is positioned at a first activation position at one end of the transducer array. The probe 20a may select the second transducer group, which is positioned at a second activation position at an opposing end of the transducer array in a lengthwise direction. The probe 20a may transmit ultrasound waves by using the transducers of a corresponding first or second transducer group at a position which has been alternately moved from the first activation position and the second activation position toward a center of the transducer array at a first movement speed. The first movement speed may be determined based on the object or the measurement result.

Figure 18:
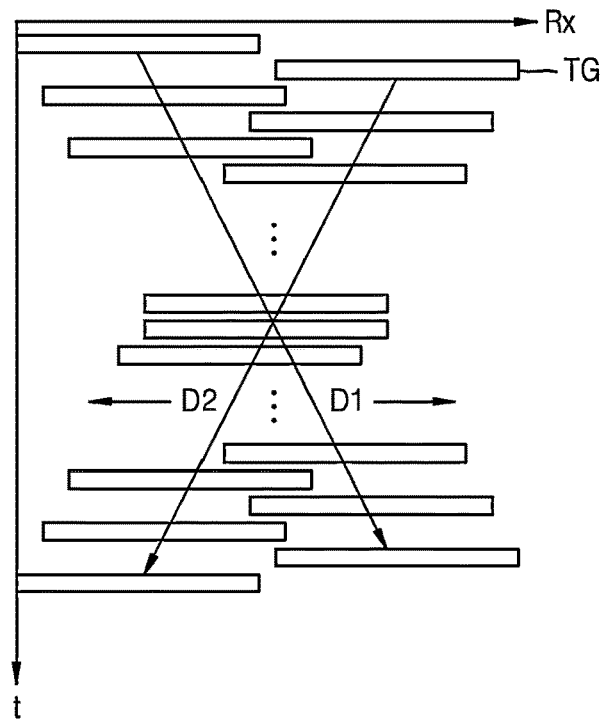
FIG. 18 is a diagram for describing a shear wave measuring operation according to an exemplary embodiment.

FIG. 18 is a diagram for describing a shear wave measuring operation according to an exemplary embodiment.

According to the present exemplary embodiment, a shear wave may be generated at a plurality of points, and the ultrasound diagnostic apparatus 1000a may obtain an echo image by alternately moving the position of the transducer group TG in a propagation direction of a shear wave in which the shear wave propagates from both ends of the probe 20a. For example, the transducer group TG may be moved in a first direction D1 in which the transducer group TG propagates from the left to the right of the probe 20a, and a second direction D2 in which the transducer group TG propagates from the right to the left. The propagation in the first direction D1 and the second direction D2 is alternately performed.

According to the present exemplary embodiment, since a shear wave that is generated at a plurality of points may be detected and a shear wave having a relatively high amplitude may be detected in any region of an image early in an echo signal detection time, a shear wave detection speed may be increased and a degree of accuracy in detecting a shear wave may be increased.

Figure 19:
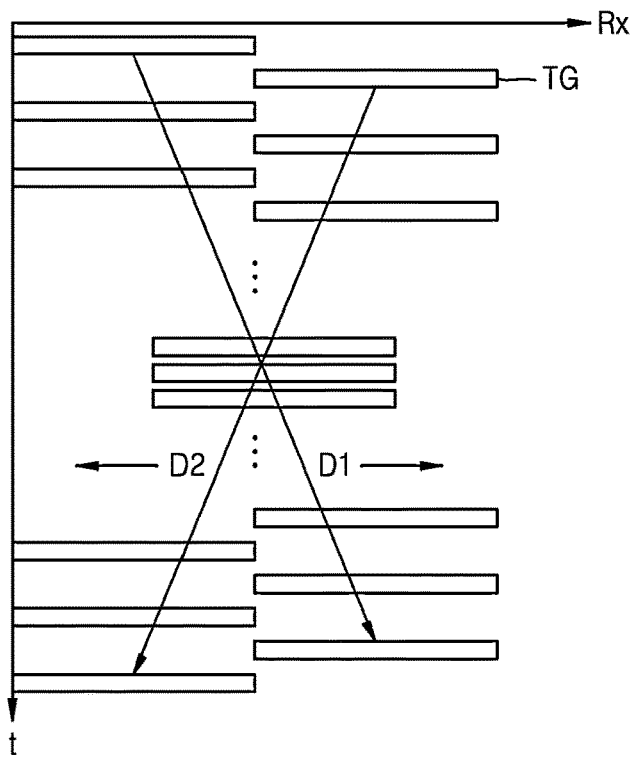
FIG. 19 is a diagram for describing a shear wave measuring operation according to an exemplary embodiment.

FIG. 19 is a diagram for describing a shear wave measuring operation according to an exemplary embodiment.

According to the present exemplary embodiment, a shear wave may be generated at a plurality of points, and an echo image may be obtained by alternately moving the transducer group TG from both ends of the probe 20a. For example, the transducer group TG may be moved in the first direction D1 in which the transducer group TG is moved from the left to the right of the probe 210, and the second direction D2 in which the transducer group TG is moved from the right to the left of the probe 20a. The propagation is alternately performed in the first direction D1 and the second direction D2. According to the present exemplary embodiment, the transducer group TG may be moved in each direction (the first direction and the second direction) after ultrasound waves are repeatedly transmitted "a" times by the same transducer group TG. Then, ultrasound waves are repeatedly transmitted "a" times by the next transducer group TG.

According to another exemplary embodiment, when a difference between a measured shear wave propagation speed and a predicted shear wave propagation speed is equal to or greater than a reference value, the ultrasound diagnostic apparatus 1000a may correct the predicted shear wave propagation speed to the measured shear wave propagation speed and may measure a shear wave propagation speed again. According to the present exemplary embodiment, propagation of a shear wave at the corrected predicted shear wave propagation speed may be more accurately imaged, thereby increasing a degree of accuracy in measuring the shear wave propagation speed.

Figure 20:
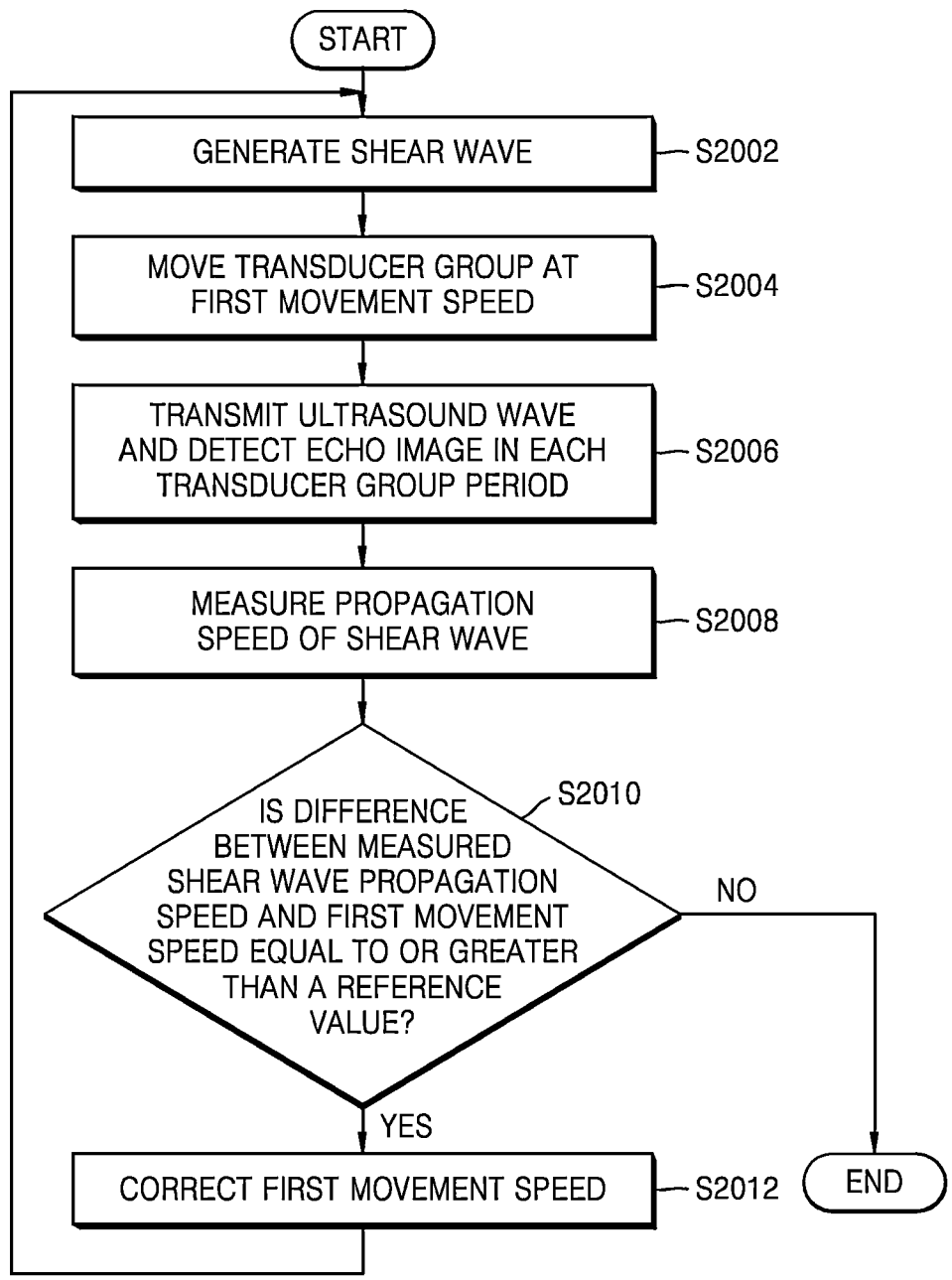
FIG. 20 is a flowchart illustrating an ultrasound image capturing method according to an exemplary embodiment.

FIG. 20 is a flowchart illustrating an ultrasound image capturing method according to an exemplary embodiment.

First, the ultrasound diagnostic apparatus 1000a transmits an ultrasound wave of a focus beam onto the object 10 by using the probe 20a to generate a shear wave in a tissue of the object 10 in operation S2002. The ultrasound diagnostic apparatus 1000a moves a transducer group (TG) at the first movement speed in operation S2004, and transmits an ultrasound wave in each transducer group period to detect an echo image in operation S2006.

The ultrasound diagnostic apparatus 1000a calculates a variation image from the echo image, determines a position of a shear wave in an image by using the variation image, and measures a propagation speed of the shear wave in operation S2008. For example, when it is determined that a difference between the measured shear wave propagation speed and the first movement speed is equal to or greater than a reference value in operation S2010, the ultrasound diagnostic apparatus 1000a may correct the first movement speed to the measured shear wave propagation speed in operation S2012, and may again measure a shear wave propagation speed by performing operations S2002, S2004, S2006, and S2008. For example, as a result of correcting the first movement speed, the transducer groups may include the same transducers as compared to the transducers included in the transducer groups prior to correcting the first movement speed. As another example, one or more of the transducer groups may include different transducers as compared to the transducers included in the transducer groups prior to correcting the first movement speed.

According to another exemplary embodiment, the ultrasound diagnostic apparatus 1000a may measure the first movement speed, and then measure a shear wave propagation speed by using the measured first movement speed. An operation of measuring the first movement speed may be performed simpler and faster than an operation of measuring the shear wave propagation speed. For example, in measuring the first movement speed, without moving a position of a selected transducer group (TG), the ultrasound diagnostic apparatus 1000a may detect propagation of a shear wave for a limited time by the same transducer group (TG), and measure the first movement speed.

Figure 21:
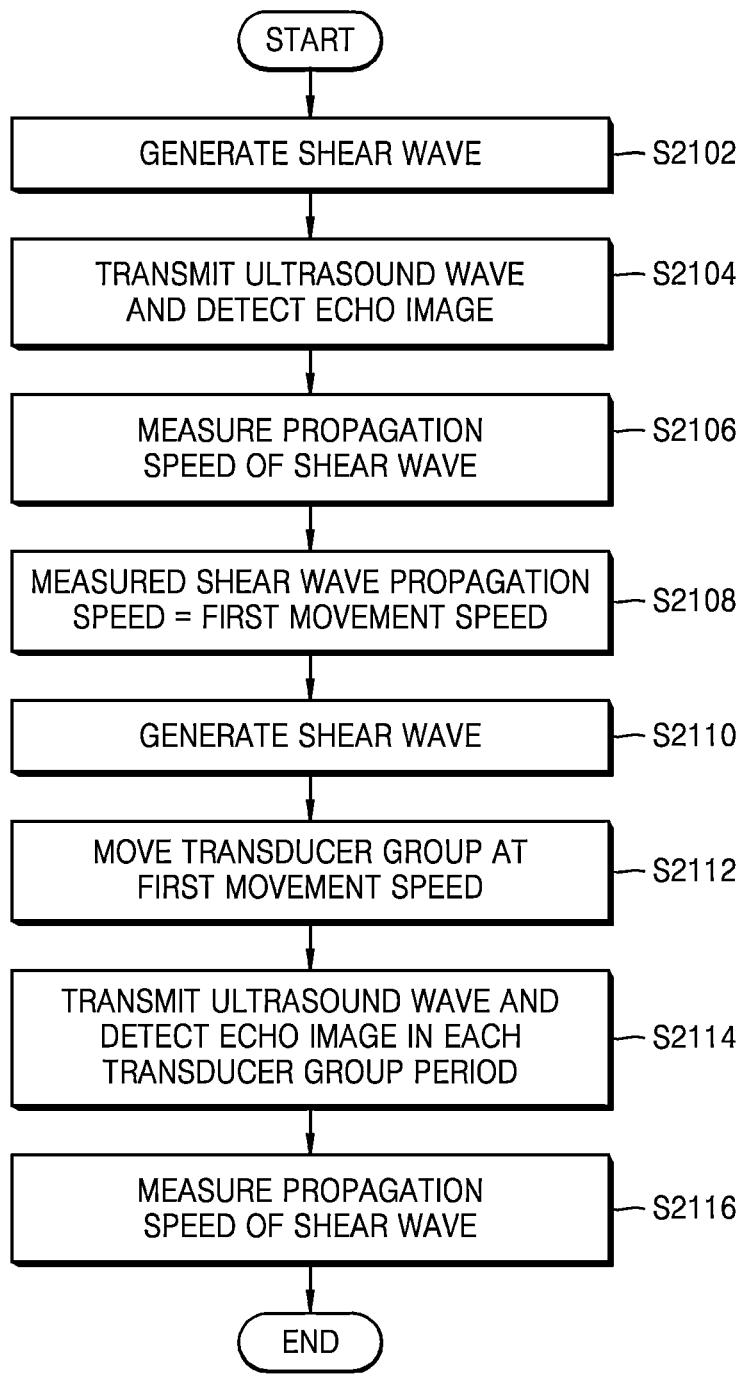
FIG. 21 is a flowchart illustrating an ultrasound image capturing method according to an exemplary embodiment.

FIG. 21 is a flowchart illustrating an ultrasound image capturing method according to an exemplary embodiment.

First, the ultrasound diagnostic apparatus 1000a transmits an ultrasound wave of a focus beam onto the object 10 by using the probe 20a to generate a shear wave in a tissue of the object 10 in operation S2102. The ultrasound diagnostic apparatus 1000a transmits an ultrasound wave onto the object 10 to detect an echo image in operation S2104, and measures a shear wave propagation speed in operation S2106. The measured shear wave propagation speed is set to the first movement speed in operation S2108. For example, in measuring the first movement speed, without moving a transducer group (TG), the ultrasound diagnostic apparatus 1000a may detect propagation of a shear wave for a limited time in a fixed transducer group (TG), and measure the first movement speed.

The ultrasound diagnostic apparatus 1000a transmits an ultrasound wave of a focus beam onto the object 10 by using the probe 20a to generate a shear wave in a tissue of the object 10 in operation S2110. The ultrasound diagnostic apparatus 1000a moves a transducer group (TG) of the transducer 310 at the first movement speed in operation S2112, and transmits an ultrasound wave in each transducer group period to detect an echo image in operation S2114.

The ultrasound diagnostic apparatus 1000a calculates a variation image from the echo image, determines a position of a shear wave in an image by using the variation image, and measures a propagation speed of the shear wave in operation S2116.

Figure 22:
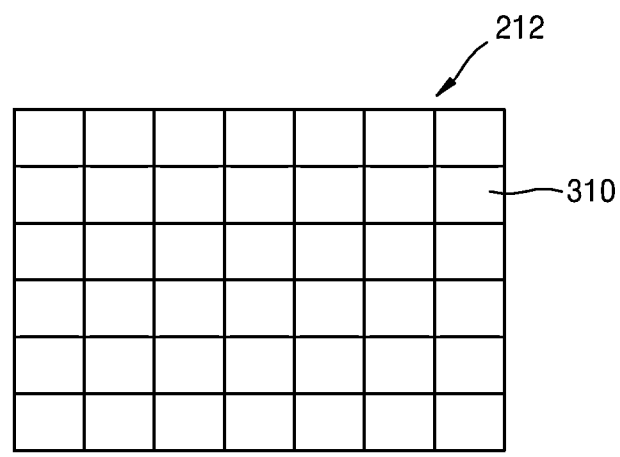
FIG. 22 is a diagram illustrating a structure of a transducer array according to an exemplary embodiment.

FIG. 22 is a diagram illustrating a structure of a transducer array 212 according to an exemplary embodiment.

According to an exemplary embodiment, the transducer array 212 may have a 1D linear structure, a 1.5D structure, or a 2D structure. For example, as illustrated in FIG. 22, a plurality of transducers may be arranged in a 2D matrix type structure. The 2D transducer array 212 may be disposed to transmit an ultrasound wave toward an object of the probe 20a.

The 2D transducer array 212 may be disposed in various types of structures such as a honeycomb type and a radial type structure, in addition to the structural type of FIG. 22. The transducer array 212 according to an exemplary embodiment may include a convex array.

Figure 23:
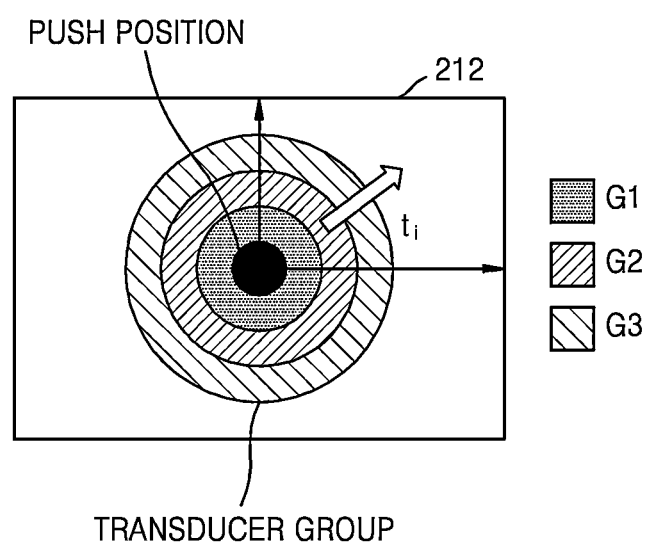
FIG. 23 is a diagram for describing a state where a position of a selected transducer group is moved in a transducer array, according to an exemplary embodiment.

FIG. 23 is a diagram for describing a state where a position of a selected transducer group is moved in a transducer array 212, according to an exemplary embodiment.

The ultrasound diagnostic apparatus 1000a according to the present exemplary embodiment, as illustrated in FIG. 23, may select a transducer group of a concentric circle type or a concentric ellipse type, in the 2D transducer array 212. For example, as illustrated in FIG. 23, a transducer group G1, a transducer group G2, and a transducer group G3 may be used. A transducer included in a transducer group of the type illustrated in FIG. 23 is activated in each activation period. A center of a concentric circle or a concentric ellipse, for example, may be determined as a push position at which a shear wave is generated.

According to another exemplary embodiment, a transducer group may be implemented as various types such as a concentric triangle, a concentric tetragon, and a concentric pentagon.

Figure 24:
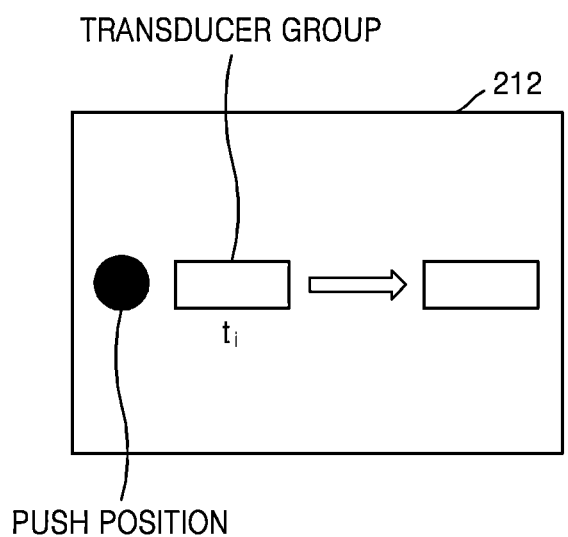
FIG. 24 is a diagram for describing a state where a position of a transducer group is moved in a transducer array, according to another exemplary embodiment.

FIG. 24 is a diagram for describing a state where a position of a transducer group is moved in a transducer array 212, according to an exemplary embodiment.

The ultrasound diagnostic apparatus 1000a according to the present exemplary embodiment, as illustrated in FIG. 24, may select a transducer group at a position which is moved in a direction (one direction) deviating from a push position, in the 2D transducer array 212. For example, as illustrated in FIG. 24, the position of the selected transducer group may propagate in a direction (in one row) deviating from the push position. The transducer group may have a 1D transducer array type in which transducers are arranged in one row or a 2D transducer array type including transducers which are arranged in a plurality of rows. The type of the transducer group may be determined as various types such as a rectangle, a square, a circle, and an ellipse. A transducer included in a transducer group of the type illustrated in FIG. 24 is activated in each activation period.

Figure 25:
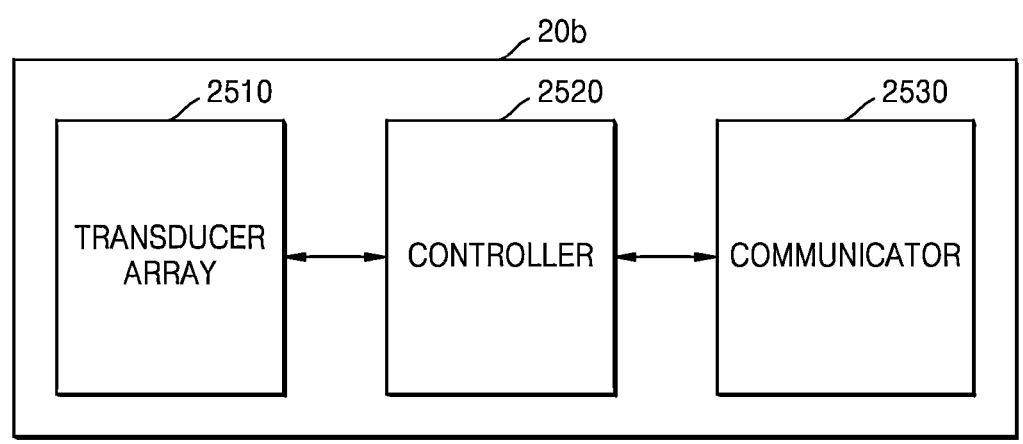
FIG. 25 is a diagram illustrating a probe according to an exemplary embodiment.

FIG. 25 is a diagram illustrating a probe 20b according to an exemplary embodiment.

The probe 20b according to the present exemplary embodiment includes a transducer array 2510, a controller 2520, and a communicator 2530.

The transducer array 2510 includes n transducers which may be arranged as a 1D array, a 1.5D array, or a 2D array.

The controller 2520 determines a first movement speed based on an object 10 or a measurement result, moves a transducer group, which is a range of m (where m>n, and m is a natural number) transducers activated among the n transducers, at the first movement speed, and transmits an ultrasound wave to detect an echo signal from the object 10 in each transducer group by using the m transducers included in the transducer group. The probe 20b itself may determine the first movement speed, based on the object 10 or the measurement result. Information (for example, the first movement speed based on the kind of object) for determining the first movement speed may be stored in the probe 20b, or may be received from another electronic device by using the communicator 2530.

The communicator 2530 transmits an echo signal to the other electronic device. Examples of the other electronic device include an electronic device such as the ultrasound diagnostic apparatus 1000a, a server, a PC, a portable terminal, or a tablet PC. The communicator 2530 communicates with the other electronic device by wire or wirelessly. For example, the communicator 2530 may include at least one of a short-distance communicator, a wired communicator, and a mobile communicator.

The short-distance communicator denotes a module for short-distance communication within a certain distance. Short-distance communication technology, according to an exemplary embodiment, may include wireless LAN, Wi-Fi, Bluetooth, Zigbee, WFD, UWB, IrDA, BLE, and NFC, but the short-distance communication technology is not limited thereto.

The wired communicator denotes a module for communication using an electrical signal or an optical signal. Wired communication technology according to an exemplary embodiment may include a paired cable, a coaxial cable, an optical fiber cable, or an Ethernet cable.

The mobile communicator transmits and receives a radio frequency (RF) signal to and from a base station, an external terminal, and a server over a mobile communication network. The RF signal may include various types of data based on transmission and reception of a voice call signal, a video call signal, or a letter/multimedia message.

According to an exemplary embodiment, the controller 2520 may generate an echo image from the detected echo signal, and transmit the echo image to the other electronic device. The other electronic device may receive the echo signal or the echo image to calculate an object change speed.

According to another exemplary embodiment, the controller 2520 may measure an object change movement speed from the detected echo signal, and the communicator 2530 may transmit information about the object change movement speed to the other electronic device. According to the present exemplary embodiment, the probe 20b itself calculates the object change movement speed while moving an activation range of transducers, and thus, a user may measure the object change movement speed conveniently and accurately. Also, according to the present exemplary embodiment, an amount of communication between the probe 20b and the other electronic device is reduced.

A method of capturing an ultrasound wave, according to one or more exemplary embodiments, may be implemented as a software module or an algorithm. Any methods may be implemented as software modules or algorithms and may be stored as program instructions or computer-readable codes executable by a processor on a computer-readable recording medium. Examples of the computer-readable recording medium include magnetic storage media (e.g., ROM, floppy disks, hard disks, etc.), optical recording media (e.g., CD-ROMs, DVDs), etc. The computer-readable recording medium can be distributed over network-coupled computer systems so that the computer-readable code is stored and executed in a distributed fashion. The recording medium may be read by the computer, stored in the memory, and executed by the processor. When the recording medium is connected to the ultrasound diagnostic apparatus 1000a, the ultrasound diagnostic apparatus 1000a may be configured to perform the method of capturing an ultrasound image, according to one or more exemplary embodiments.

The foregoing exemplary embodiments and advantages are merely exemplary and are not limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An ultrasound diagnostic apparatus comprising:
   a probe that comprises a transducer array comprising transducers configured to transmit ultrasound waves to an object, and to detect echo signals reflected by the object in response to the ultrasound waves; and
   a controller coupled to the probe and configured to generate echo images from the echo signals, to acquire, from the echo images, a first movement speed at which a target in the object moves, and to select a number of the transducers to be activated as a first transducer group and a number of the transducers to be activated as a second transducer group based on the first movement speed,
   wherein the controller is further configured to:
      control the probe to transmit a first ultrasound wave, among the ultrasound waves, by at least one first transducer included in the first transducer group disposed at a first activation position and detect the echo signals reflected from the object, and to transmit a second ultrasound wave, among the ultrasound waves, by at least one second transducer included in the second transducer group disposed at a second activation position and detect the echo signals reflected from the object, the second activation position being spatially moved from the first activation position at the first movement speed in a first direction in which the target in the object moves,
      generate a variation image based on the echo images acquired from the echo signals detected in response to transmitting the first ultrasound wave and the second ultrasound wave, and
      calculate, from the variation image, a second movement speed, at which the target in the object moves in the first direction.

2. The ultrasound diagnostic apparatus of claim 1, wherein the controller is further configured to control the probe is further configured to transmit the second ultrasound wave after a lapse of a time interval after the first ultrasound wave is transmitted.

3. The ultrasound diagnostic apparatus of claim 1, wherein the ultrasound waves transmitted by the probe comprise ultrasound plane waves.

4. The ultrasound diagnostic apparatus of claim 1, wherein the controller is further configured to control the probe to move an ultrasound wave transmission position of a focused beam within each of the first transducer group and the second transducer group, to transmit the first ultrasound wave and the second ultrasound wave of the focused beam onto the object by the at least one first transducer and the at least one second transducer, and to detect the echo signals corresponding to the ultrasound wave transmission position of the focused beam.

5. The ultrasound diagnostic apparatus of claim 1, wherein the controller is further configured to:
correct the first movement speed in response to a difference between the second movement speed and the first movement speed being equal to or greater than a reference value, and
control the probe to transmit the second ultrasound wave by at least one of the transducers included in the second transducer group at another second activation position which has been spatially moved from the first activation position at the corrected first movement speed, to detect corrected echo signals reflected from the object based on the corrected first movement speed, and to re-calculate the second movement speed based on the corrected echo signals.

6. The ultrasound diagnostic apparatus of claim 1, wherein the controller is further configured to calculate the variation image from two of the echo images which are sequentially captured, to detect a change position of the target from the variation image, and to calculate the second movement speed by using the change position of the target.

7. The ultrasound diagnostic apparatus of claim 1, wherein the probe further comprises multiplexers that connect selected transducers to a signal transfer channel connected to the controller, and
the at least one first transducer and the at least one second transducer are the selected transducers which are selected by the multiplexers.

8. The ultrasound diagnostic apparatus of claim 1, wherein the controller is further configured to control the probe to transmit the ultrasound waves onto the object to generate a shear wave in the object,
the target in the object comprises the shear wave, and
the second movement speed comprises a propagation speed of the shear wave.

9. The ultrasound diagnostic apparatus of claim 8, wherein the controller is further configured to control the probe to transmit the ultrasound waves of a focused beam onto the object to generate the shear wave.

10. The ultrasound diagnostic apparatus of claim 8, wherein the controller is further configured to control the probe to generate the shear wave at a plurality of points of the object.

11. The ultrasound diagnostic apparatus of claim 10, wherein the transducers of the transducer array are further configured to be activated as a third transducer group and as a fourth transducer group, and the controller is further configured to:
select a number of the transducers to be activated in the third transducer group and a number of the transducers to be activated in the fourth transducer group based on the first movement speed,
select the first transducer group to include the transducers disposed at one end of the transducer array,
select the third transducer group to include the transducers disposed at an opposing end of the transducer array in a lengthwise direction of the transducer array, and calculate the second movement speed by controlling the probe to transmit the ultrasound waves by using the transducers at a position which is alternately moved from the one end of the transducer array and the opposing end of the transducer array toward a center of the transducer array at the first movement speed, by the controlling comprising controlling the probe to transmit a third ultrasound wave, among the ultrasound waves, by the at least one third transducer included in the third transducer group after the first ultrasound wave is transmitted, transmit the second ultrasound wave after the third ultrasound wave is transmitted, and transmit a fourth ultrasound wave, among the ultrasound waves, by the at least one fourth transducer included in the fourth transducer group after the second ultrasound wave is transmitted, and detect detecting the echo signals from the object.

12. A method for capturing an ultrasound image, the method comprising:
transmitting, by transducers of a transducer array of an ultrasonic probe, ultrasound waves to an object, and detecting echo signals reflected by the object in response to the ultrasound waves;
generating echo images from the echo signals;
acquiring, from the echo images, a first movement speed at which a target in the object moves;
selecting a number of the transducers to be activated as a first transducer group and a number of the transducers to be activated as a second transducer group, based on the first movement speed;
transmitting a first ultrasound wave onto the object, among the ultrasound waves, by at least one first transducer included in the first transducer group disposed at a first activation position and detecting the echo signals reflected from the object;
transmitting a second ultrasound wave onto the object, among the ultrasound waves, by at least one second transducer included in the second transducer group disposed at a second activation position and detecting the echo signals reflected from the object, the second activation position being spatially moved from the first activation position at the first movement speed in a first direction in which the target in the object moves;
generating a variation image based on the echo images acquired from the echo signals detected in response to the transmitting the first ultrasound wave and the second ultrasound wave; and
calculating, from the variation image, a second movement speed, at which the target in the object moves in the first direction.

13. The method of claim 12, wherein the step of transmitting the second ultrasound wave comprises:
transmitting the second ultrasound wave after a lapse of a time interval after the transmitting the first ultrasound wave.

14. The method of claim 12, wherein the ultrasound waves transmitted into the object comprise ultrasound plane waves.

15. The method of claim 12, wherein the steps of transmitting the first ultrasound wave and the transmitting the second ultrasound wave comprise:
while moving an ultrasound wave transmission position of a focused beam within each of the first transducer group and the second transducer group, transmitting the first ultrasound wave and the second ultrasound wave of the focused beam onto the object by using the at least one first transducer and the at least one second transducer, and wherein the detecting the echo signals comprises detecting the echo signals corresponding to the ultrasound wave transmission position of the focused beam.

16. The method of claim 12, further comprising:

correcting the first movement speed in response to a difference between the second movement speed and the first movement speed being equal to or greater than a reference value;

transmitting the second ultrasound wave by at least one of the transducers included in the second transducer group at another second activation position which has been spatially moved from the first activation position at the corrected first movement speed, to detect corrected echo signals from the object based on the corrected first movement speed; and re-calculating the second movement speed based on the corrected echo signals.

17. The method of claim 12, wherein the generating the variation image comprises calculating the variation image from two of the echo images which are sequentially captured, and the calculating the second movement speed comprises:
  detecting a change position of the target from the variation image; and
  calculating the second movement speed by using the change position of the target.

18. The method of claim 12, further comprising:

providing multiplexers that connect selected transducers to a signal transfer channel, wherein the at least one first transducer and the at least one second transducer are the selected transducers which are selected by the multiplexers.

19. The method of claim 12, wherein the transmitting the ultrasound waves further comprises generating a shear wave in the object, the target in the object comprises the shear wave, and
the second movement speed is a propagation speed of the shear wave.

20. The method of claim 19, wherein the generating the shear wave further comprises transmitting the ultrasound waves of a focused beam onto the object.

21. The method of claim 19, wherein the generating the shear wave further comprises generating the shear wave at a plurality of points in the object.

22. The method of claim 21, wherein the selecting comprises:

selecting a number of the transducers of the transducer array to be activated in a third transducer group and a number of the transducers of the transducer array to be activated in a fourth transducer group, selecting, as the first transducer group, the transducers disposed at a first end of the transducer array, in a lengthwise direction of the transducer array, and selecting, as the third transducer group, the transducers disposed at a second end of the transducer array in the lengthwise direction, the second end opposing the first end, wherein the calculating the second movement speed comprises controlling the ultrasonic probe to transmit the ultrasound waves by using the transducers at a position which is alternately moved from the first end of the transducer array and the second end of the transducer array toward a center of the transducer array at the first movement speed, and to detect detecting the echo signals from the object, wherein the controlling the ultrasonic probe comprises controlling the ultrasonic probe to transmit a third ultrasound wave, among the ultrasound waves, by at least one third transducer included in the third transducer group after the first ultrasound wave is transmitted, to transmit the second ultrasound wave after the third ultrasound wave is transmitted, and to transmit a fourth ultrasound wave, among the ultrasound waves, by at least one fourth transducer included in the fourth transducer group after the second ultrasound wave is transmitted.

23. A probe comprising:

a transducer array that comprises transducers configured to transmit ultrasound waves to an object, and to detect echo signals reflected by the object in response to the ultrasound waves; and a controller coupled to the transducers and configured to generate echo images from the echo signals, to acquire, from the echo images, a first movement speed at which a target in the object moves, and to select a number of the transducers to be activated as a first transducer group and a number of the transducers to be activated as a second transducer group, based on the first movement speed, wherein the controller is further configured to control at least one first transducer included in the first transducer group disposed at a first activation position to transmit a first ultrasound wave onto the object, among the ultrasound waves, and detect the echo signals reflected from the object, and to control at least one second transducer included in the second transducer group disposed at a second activation position to transmit a second ultrasound wave onto the object, among the ultrasound waves, and detect the echo signals reflected from the object, the second activation position being spatially moved from the first activation position at the first movement speed in a first direction in which the target in the object moves, and wherein the probe further comprises a communicator coupled to the controller and configured to transmit the echo signals to an electronic device configured to generate a variation image based on the echo images acquired from the echo signals detected by the at least one first transducer and the at least one second transducer, and to calculate, from the variation image, a second movement speed, at which the target in the object moves in the first direction.

24. A non-transitory computer-readable recording medium storing computer program codes which, when executed by a computer, cause the computer to execute a method of capturing an ultrasound image, the method comprising:

transmitting, by transducers of a transducer array of an ultrasonic probe, ultrasound waves to an object, and detecting echo signals reflected by the object in response to the ultrasound waves;

generating echo images from the echo signals;

acquiring, from the echo images, a first movement speed at which a target in the object moves;

selecting a number of the transducers to be activated as a first transducer group and a number of the transducers to be activated as a second transducer group, based on the first movement speed;

transmitting a first ultrasound wave onto the object, among the ultrasound waves, by at least one first transducer included in the first transducer group disposed at a first activation position and detecting the echo signals reflected from the object;

transmitting a second ultrasound wave onto the object, among the ultrasound waves, by at least one second transducer included in the second transducer group disposed at a second activation position and detecting the echo signals reflected from the object, the second activation position being spatially moved from the first activation position at the first movement speed in a first direction in which the target in the object moves;

generating a variation image based on the echo images acquired from the echo signals detected in response to the transmitting the first ultrasound wave and the second ultrasound wave; and calculating, from the variation image, a second movement speed at which the target in the object moves in the first direction.

25. The ultrasound diagnostic apparatus of claim 1, wherein a first transmission start time of the at least one first transducer and a second transmission start time of the at least one second transducer are staggered in correspondence with the first movement speed, and as a value of the first movement speed becomes greater, a delay between the first transmission start time and the second transmission start time becomes shorter, or a distance, along the transducer array, between a position of the at least one first transducer and a position of the at least one second transducer becomes longer.

26. The ultrasound diagnostic apparatus of claim 1, wherein the first movement speed, at which the second activation position is moved, substantially coincides with the second movement speed.

\* \* \* \* \*